United States Patent [19]
Henkin et al.

[11] Patent Number: 5,398,675
[45] Date of Patent: Mar. 21, 1995

[54] ANESTHESIA REBREATHING SYSTEM

[76] Inventors: Melvyn L. Henkin, 5011 Donna Ave., Tarzana, Calif. 91356; Jordan M. Laby, 3038 Bayshore, Ventura, Calif. 93001

[21] Appl. No.: 960,935

[22] Filed: Oct. 14, 1992

[51] Int. Cl.⁶ ............................................. A61M 15/00
[52] U.S. Cl. .......................... 128/203.12; 128/203.28; 128/205.15
[58] Field of Search ...................... 128/203.12, 203.28, 128/205.12, 205.24, 205.17, 205.15, 909, 910

[56] References Cited

U.S. PATENT DOCUMENTS

| | | | |
|---|---|---|---|
| 3,814,091 | 6/1974 | Henkin | 128/202.22 |
| 3,831,595 | 8/1974 | Valenta et al. | 128/202.22 |
| 3,901,230 | 8/1975 | Henkin | 128/205.17 |
| 3,973,564 | 8/1976 | Carden | 128/205.14 |
| 4,020,834 | 5/1977 | Bird | 128/205.14 |
| 4,051,847 | 10/1977 | Henkin | 128/202.22 |
| 4,676,239 | 6/1987 | Humphrey | 128/911 |
| 4,991,576 | 2/1991 | Henkin et al. | 128/203.28 |

*Primary Examiner*—Edgar S. Burr
*Assistant Examiner*—Aaron J. Lewis
*Attorney, Agent, or Firm*—Freilich Hornbaker Rosen

[57] ABSTRACT

An anesthesia gas delivery system including a patient circuit implemented primarily by a detachable structural portion and a control system implemented primarily by a permanent structural portion. The patient circuit includes a variable volume patient reservoir and a patient overflow tube. The control system includes a subsystem for preventing gas flow out of the overflow tube until the patient reservoir is full except when a pediatric breathing circuit is being used.

21 Claims, 11 Drawing Sheets

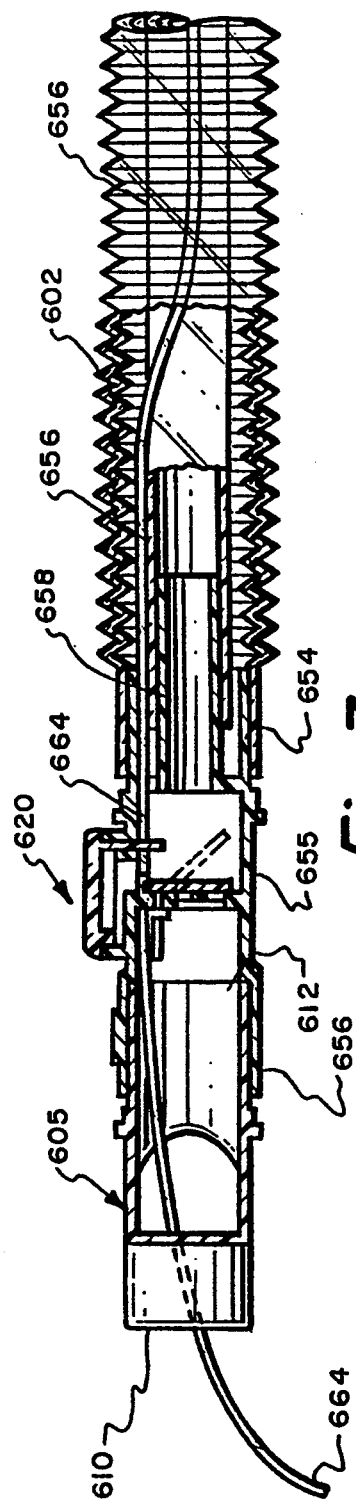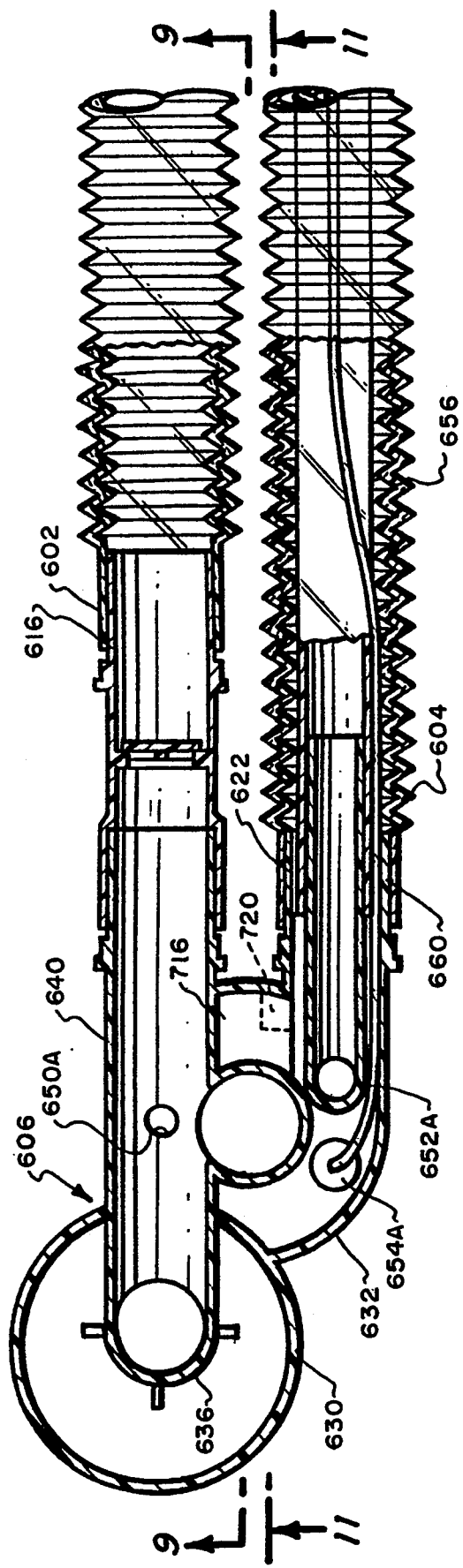

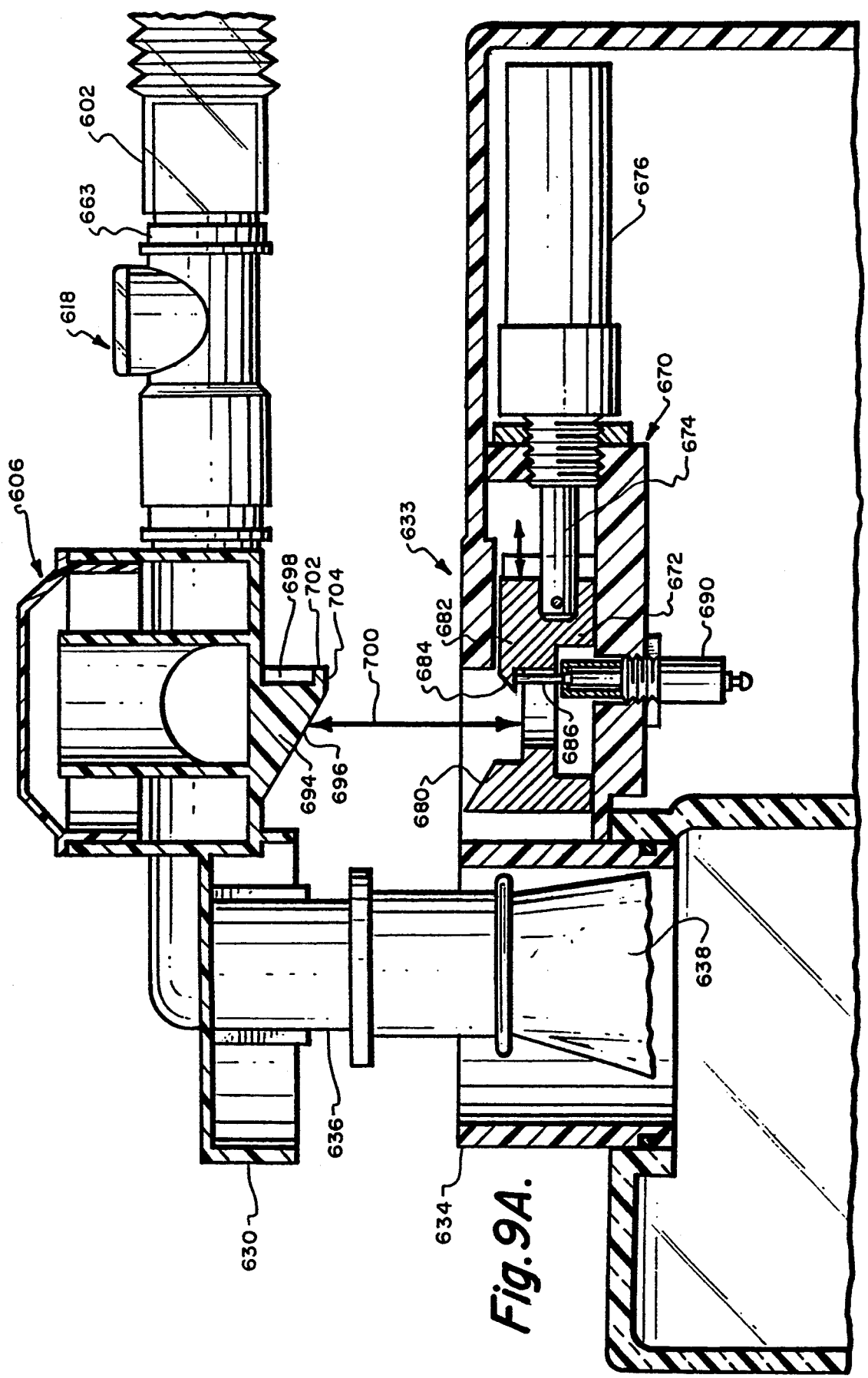

ANESTHESIA REBREATHING SYSTEM

FIELD OF THE INVENTION

This invention relates generally to systems for administering anesthesia gas to medical patients.

BACKGROUND OF THE INVENTION

U.S. Pat. Nos. 3,814,091 and 3,901,230 disclose anesthesia rebreathing systems characterized by a geometry which preferentially vents expired alveolar gas, rich in carbon dioxide ($CO_2$), while retaining fresh gas and initially expired dead space gas, rich in oxygen ($O_2$), for rebreathing by the patient to thus minimize the need for $CO_2$ absorption. More particularly, the systems comprise a patient circuit incorporating an overflow tube whose entrance is located very close to the patient. The overflow tube exits at a patient overflow (commonly referred to as "Pop-Off") valve which is located close to an anesthesia machine where it can be conveniently controlled by an attending anesthetist. By locating the overflow tube entrance close to the patient, it functions to preferentially vent alveolar gas through the patient overflow (i.e. Pop-Off) valve and save dead space and unbreathed gas within the tubing and reservoir of the patient circuit. The Pop-Off valve is operable in two different modes, i.e., (1) as a manually controlled variable orifice for spontaneous, manually assisted or controlled ventilation and (2) as an automatically Controlled Valve responding to a positive control pressure for manually assisted or controlled ventilation or mechanically controlled ventilation.

The enhanced system described in U.S. Pat. No. 3,901,230 can be viewed as functionally including (1) a patient circuit and (2) a ventilator/isolator (V/I) circuit for controlling gas volume and pressure in the patient circuit. The preferred embodiment can be viewed as structurally including (1) a single use portion and (2) a reusable portion. The embodiment is configured so that the single use portion forms most of the patient circuit with the reusable portion forming the V/I circuit and part of the patient circuit, e.g. the patient Pop-Off Valve. The V/I circuit includes a constant volume (e.g. rigid) container (forming part of the system's reusable portion) within which a variable volume patient breathing reservoir (e.g. a flaccid bag) (forming part of the single use portion) is accommodated. The pressure within the rigid container is controlled (1) during manually assisted or controlled ventilation, by an attending anesthetist squeezing an outside bag and (2) during mechanically controlled ventilation by a conventional MECHANICAL VENTILATOR. The pressure variations in the rigid container are applied to the patient circuit via the flexible walls of the patient bag. Cross-contamination is eliminated in the disclosed preferred embodiment because the patient expired gas cannot come into contact with the reusable portion components exposed to inspired gas.

U.S. Pat. No. 4,991,576 discloses an anesthesia rebreathing system which retains the advantages of the systems disclosed in U.S. Pat. Nos. 3,814,091 and 3,901,230 and which incorporates additional features to enhance ease of use and safe operation.

In accordance with U.S. Pat. No. 4,991,576, instead of using multiple independently operable user controls, an integrated control knob is provided whose position determines the system operating mode. Thus, in a first disclosed embodiment, the user control knob can be rotated to any one of the following mutually exclusive positions:
1. AUXILIARY OUTLET
2. OFF
3. MECHANICAL VENTILATOR MODE
4. MANUAL BAG MODE Position 3 is used to ventilate the patient with a MECHANICAL VENTILATOR. Position 4 is used to allow the patient to breath spontaneously or to manually control or assist ventilation. In a second disclosed embodiment, the four aforementioned positions are supplemented by an automatic bag mode position (i.e. position 5) at which the system self adjusts without requiring Manual Valve adjustment of a V/I Circuit Overflow Valve during spontaneous and manually assisted or controlled ventilation.

The first and second embodiments of U.S. Pat. No. 4,991,576 additionally differ from one another in that the first embodiment uses overflow gas from the patient circuit as working gas for the V/I circuit. In the second embodiment, V/I working gas is derived from a high pressure gas source (preferably dry medical grade oxygen).

The preferred single use portion of U.S. Pat. No. 4,991,576 includes a connector body configured to be detachably seated on the reusable portion for operative mating to the V/I circuit. A sensor means is coupled to the aforementioned control knob for preventing it from being moved to any of the aforementioned ventilating mode positions unless the connector body is properly seated on the reusable portion. Latching means configured to allow the connector body to be readily manually seated prevent it from being inadvertently unseated while the system is in a ventilating mode. In order to unseat (i.e., detach) the latched connector body, an unlatching means, operably coupled to the control means and actuatable only when the control knob is not in a ventilating mode position, e.g. the off position, functions to both unlatch and eject the connector body.

SUMMARY OF THE INVENTION

The present invention is directed to improvements applicable to anesthesia rebreathing systems generally, and particularly suited for use in systems of the type described in U.S. Pat. No. 4,991,576, to enhance ease of use, safe operation, and efficient use of anesthesia gas.

In accordance with a significant feature of the present invention, a control subsystem is incorporated into an anesthesia rebreathing system to maintain the patient overflow (i.e., Pop-Off) Valve closed until the patient breathing reservoir (e.g., flaccid bag) is full. As a consequence, loss of patient exhaled dead space gas and fresh gas will be minimized. In a preferred embodiment, this control subsystem includes a pneumatic cylinder for holding the patient Pop-Off Valve closed. The pneumatic cylinder is controlled by a full-bag sensor which detects when the patient breathing bag is full.

In accordance with a preferred embodiment, the full-bag sensor comprises a lever arm mounted adjacent to the patient bag and biased to a first position. As the volume of the patient bag increases, its wall engages the lever arm to move it from its first position to a second or full-bag position. The lever, in turn, operates a valve (e.g. directly or via a switch) which controls the aforementioned pneumatic cylinder.

The aforedescribed patient Pop-Off Valve control subsystem significantly improves the efficiency of fresh anesthesia gas usage at adult patient breathing rates. However, for infants and small children who breathe smaller volumes, pediatric breathing circuits comprised of smaller breathing tubes and bags are generally used. When using such pediatric breathing circuits, it may be desirable to disable the Pop-Off Valve control subsystem to reduce the pressure required to fill the patient bag. Accordingly, in accordance with a further feature of the invention, sensor means are provided for detecting which type of breathing circuit is seated on the reusable, i.e., permanent, portion and for disabling the aforementioned Pop-Off Valve control subsystem when a pediatric circuit is seated.

The embodiment described in U.S. Pat. No. 4,991,576 includes a positive end expiratory pressure (PEEP) subsystem comprising a PEEP valve in the V/I circuit against which a patient exhales. An improved PEEP subsystem in accordance with the present invention includes a second PEEP valve, incorporated in the patient overflow, i.e., Pop-Off Valve path. In use, as the patient exhales, gas flows into the patient bag forcing gas out of the rigid container through the first mentioned PEEP valve, thus establishing an initial PEEP level against which the patient exhales. This level is maintained until the patient bag is full and the Pop-Off Valve opens resulting in a reduction in PEEP level attributable to the first PEEP valve. The incorporation of a second PEEP valve in the patient overflow path in accordance with the present invention, set to the same pressure level as the first PEEP valve, serves to maintain the initial PEEP level because once the patient bag is full, the remainder of the exhalation flows through the patient overflow path.

In accordance with a further feature of the invention, a default flow path is provided for directing fresh gas inflow from an anesthesia machine to a scavenging port when the gas is not otherwise directed by the mode control knob, e.g. when the control knob is between positions. This feature prevents overpressurizing, and possibly damaging connected anesthesia machine components.

BRIEF DESCRIPTION OF THE FIGURES

FIG. 7 is a sectional view taken substantially along the plane 7—7 of FIG. 6;

FIG. 8 is a sectional view taken substantially along the plane 8—8 of FIG. 6 showing an adult patient circuit;

FIGS. 9A and 9B are sectional views taken substantially along the plane 9—9 of FIG. 8 showing the proximal end of the inspiratory tube, respectively, ready for mounting, and mounted, on the permanent portion mounting structure;

DETAILED DESCRIPTION OF THE FIGURES

Inasmuch as preferred embodiments of the present invention are similar in many respects to the embodiments disclosed in Applicants' prior U.S. Pat. No. 4,991,576, the description herein will focus primarily on the features which distinguish the present invention. Although these features, e.g., full patient reservoir sensing and pediatric breathing circuit sensing, will be described with reference to the embodiments of said U.S. Pat. No. 4,991,576, it is pointed out they are equally applicable to variety of anesthesia gas delivery systems.

Figure 1:
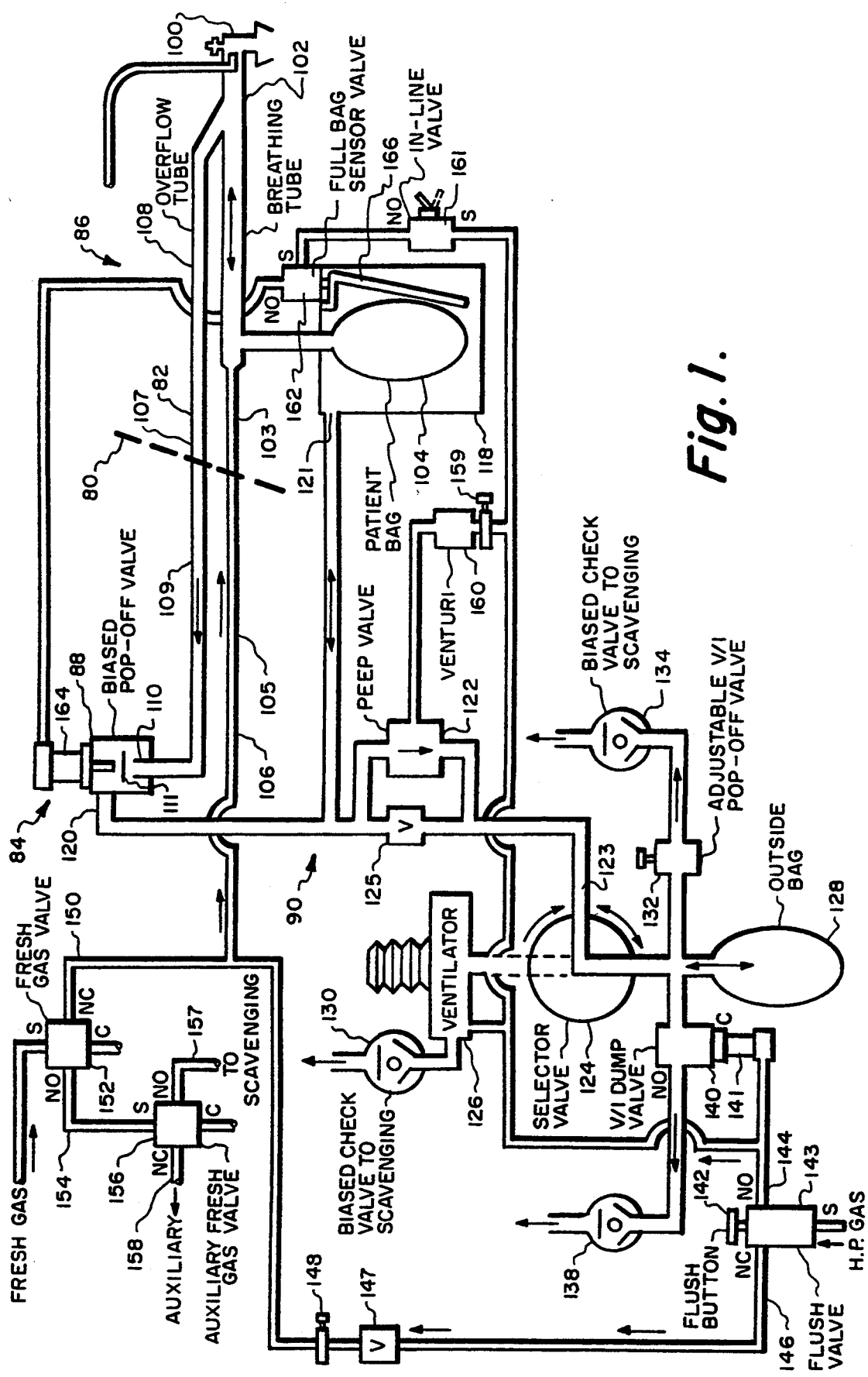
FIG. 1 is a block diagram of a first system embodiment in accordance with the present invention depicted in greater detail in FIG. 3.

Attention is now directed to FIG. 1 which is a block diagram of a first preferred system embodiment in accordance with the present invention. Note that the dashed line 80 is intended to represent the physical interface between the system's detachable (single use or sterizable) structural portion 82 and permanent structural portion 84. The detachable portion 82 includes most of the components forming the functional patient circuit 86. However, a Biased Check Valve 88 (which functions as the patient overflow (Pop-Off) Valve and may be functionally viewed as part of the patient circuit 86) is physically included in the system's permanent portion 84. The permanent portion 84 primarily comprises a ventilator/isolator (V/I) circuit or subsystem 90 for controlling the gas volume and pressure in the patient circuit 86.

Safe and reliable control of the patient circuit 86 involves several aspects. Firstly, it is extremely important for the patient circuit to be controlled so as to avoid overpressurization which could damage a patient's lungs. Secondly, it is also essential that a sufficient supply of gas of the proper composition always be available for patient inspiration. Thirdly, it is important that the control subsystem 90 provide the anesthetist with a means for rapidly initializing or readjusting the gas volume and pressure in the patient circuit 86. Additionally, it is important that the control subsystem 90 provide the mechanism whereby the patient circuit 86 can be operated either in a spontaneous, a manually assisted or controlled, or a MECHANICAL VENTILATOR ventilation mode.

Before describing the system of FIG. 1, it is pointed out that throughout this application, valves will frequently be represented as blocks having multiple ports respectively represented by the following nomenclature:

S=Supply
C=Control
NO=Normally Open
NC=Normally Closed

Figure 2:
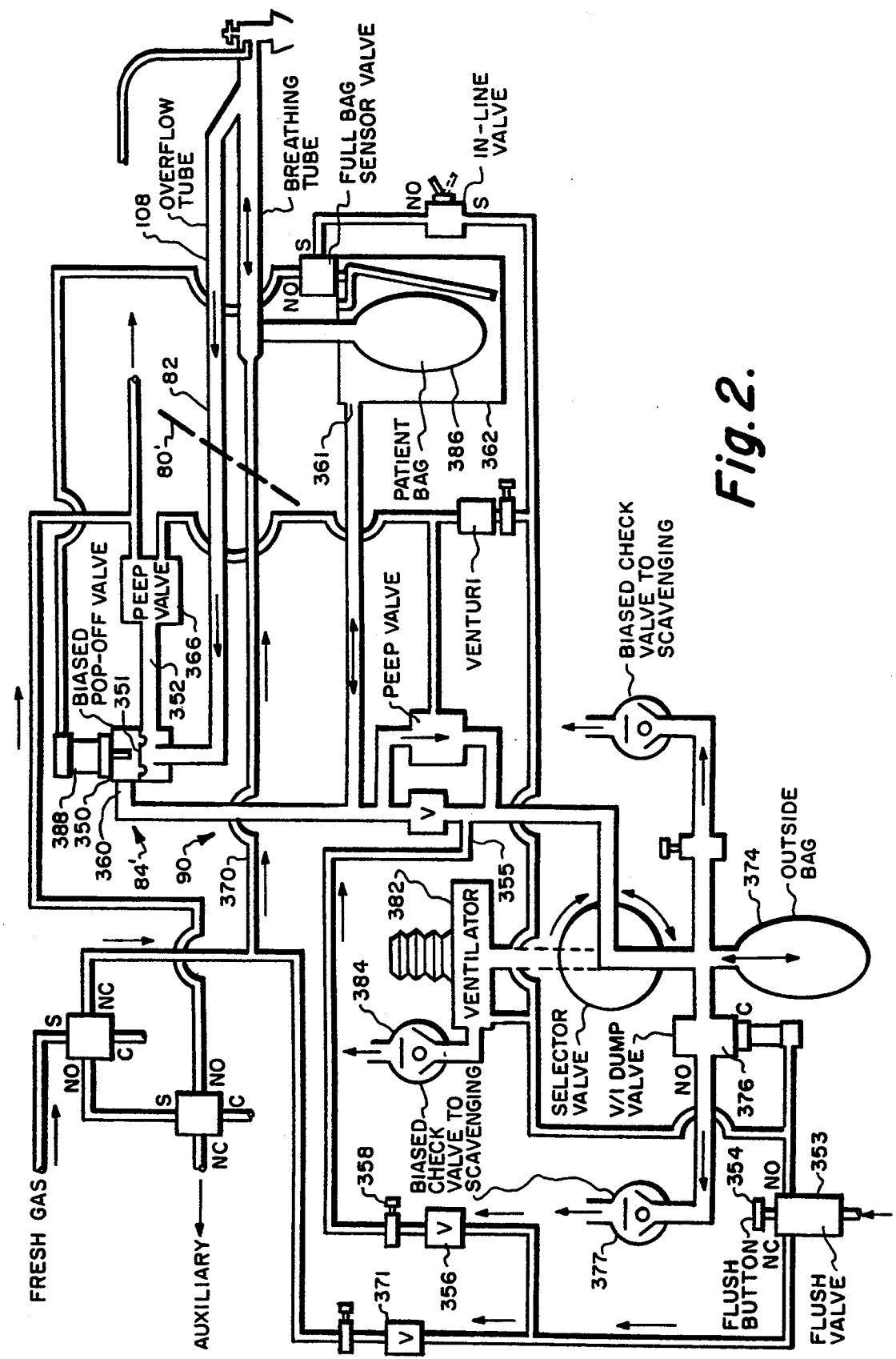
FIG. 2 is a block diagram of a second system embodiment in accordance with the present invention depicted in greater detail in FIG. 4.

In the absence of an input (e.g., pneumatic, mechanical) to a control port C, gas flow into an S port will flow out of an NO port. In the presence of an input to a control port C, gas flow into an S port will flow out of an NC port. As will be seen hereinafter in the discussion of the preferred implementations of FIGS. 3 and 4, the control inputs to various valves are dependent on the position of a mode control knob which is manually set by an attending anesthetist, i.e., user. Tables I (A and B) and II (A and B), set forth hereinafter, respectively describe the operation of FIGS. 3 and 4 for each operational mode, i.e. control knob position. The block diagrams of FIGS. 1 and 2 are more general and do not distinguish between the various operational modes.

The detachable portion 82 depicted in FIG. 1 is comprised of a device for communicating with a patient's airway, e.g., an elbow fitting 100 adapted to be coupled to a patient mask or endotracheal tube. The fitting 100 communicates with a breathing tube 102 which is shown as including a single limb for both expiratory and inspiratory gas movement but which can comprise separate inspiratory and expiratory tubes. The distal end of the breathing tube 102 is connected to the elbow fitting 100. The proximal end of the breathing tube 102 defines a fresh gas interface port 103 which is connected to a fresh gas interface port 105 on the permanent portion across the interface 80. A variable volume patient breathing reservoir, e.g., bag 104 communicates with breathing tube 102 close to the interface port 103. The permanent portion fresh gas interface port 105 opens to a fresh gas supply line 106. The detachable portion 82 additionally includes an overflow tube 108 having a tube entrance located close to the patient, i.e. fitting 100. The proximal end of the overflow tube 108 at interface port 107 is connected to an interface port 109 across the interface 80. Interface port 109 opens to inlet port 110 of the Pop-Off Valve 88 which controls gas overflow from the patient circuit 86. The Pop-Off Valve 88 is implemented by Check Valve element 111 slightly biased closed against a valve seat (not shown) represented by inlet port 110.

The V/I circuit 90 includes a constant volume, e.g., rigid, container 118 in which the patient bag 104 is removably accommodated. Changes in pressure within the container 118 are transferred to the patient circuit 86 via the flexible walls of the patient bag 104. Increases or decreases in gas volume within the patient bag are reflected by gas movement out of or into the rigid container 118.

Whereas the gas inlet to the patient Pop-Off Valve 88 is coupled to the proximal end of the overflow tube 108, the Pop-Off Valve Gas Outlet 120 is coupled to the opening 121 to rigid container 118 and, via PEEP valve 122, to a port 123 of Selector Valve 124. The port 123 is additionally coupled, via Check Valve 125 to the aforementioned Pop-Off Valve Outlet 120.

The Selector Valve 124 is operable to connect either a MECHANICAL VENTILATOR 126 or an outside bag 128 to the port 123. A Biased Check Valve 130 is intended to couple VENTILATOR 126 to an operating room scavenging system (not shown). The mouth of the outside bag 128 is coupled, via adjustable V/I overflow (Pop-Off) Valve 132, to Biased Check Valve 134, leading to the scavenging system to control gas overflow from the V/I circuit. The mouth of outside bag 128 also communicates with a Biased Check Valve 138 via a V/I Dump Valve 140 controlled by pneumatic cylinder 141. When the cylinder 141 is pressurized, it holds Dump Valve 140 closed so that the Check Valve 138 is functionally absent. When a user presses flush button 142, Flush Valve 143 cuts off high pressure gas flow to NO port 144, thus depriving cylinder 141 of its gas supply and opening Dump Valve 140. This allows Check Valve 138 to open to vent the V/I circuit and permit its bias to establish the gas volume and pressure in the V/I circuit 90. Pressing flush button 142 also supplies high pressure gas via NC port 146 to the fresh gas line 106 via Check Valve 147 and Needle Valve 148. This flushes gas through the patient circuit, Pop-Off Valve 88 and via port 123 to Biased Check Valve 138. Thus, pressing flush button 142 also establishes an initialized gas pressure and volume in patient circuit 86, as well as V/I circuit 90.

The fresh gas line 106 is normally supplied with fresh gas from an anesthesia machine (not shown) via NC port 150 of a Fresh Gas Valve 152. The NO port 154 of valve 152 supplies an Auxiliary Fresh Gas Valve 156 which selectively steers the supplied gas flow either to the scavenging system via NO port 157 or to an Auxiliary Fresh Gas Outlet via NC port 158. Thus, note that in the absence of a control input to either valve 152 or 156, the default path for the fresh gas from the anesthesia machine will be to the scavenging system.

High pressure gas flowing out of the Flush Valve 143 NO port 144 is supplied to the VENTILATOR 126, and via Needle Valve 159 and venturi 160 to the aforementioned PEEP valve 122 to set its pressure level. The flow path out of Flush Valve NO port 144 also flows through normally open In-Line Valve 161 to the Full Bag Sensor Valve 162 and then to a valve closure device, i.e., pneumatic cylinder 164. When high pressure gas is supplied to cylinder 164, it acts to hold down patient Pop-Off Valve element 111 to seal port 110 and prevent overflow from overflow tube 108 whenever the patient bag 104 is not full. This results in more efficient use of fresh anesthesia gas. When the bag 104 is full, a sensing device comprised of lever arm 166 is engaged to open the Full Bag Sensor Valve 162 to cut off the gas supply to cylinder 164, thus enabling Pop-Off Valve element 111 to operate unimpeded by cylinder 164. The In-Line Valve 161 is normally open when a detachable adult patient circuit 82 is seated on the permanent portion 84. On the other hand, when a pediatric breathing circuit is in use, the valve 161 is held closed thus preventing gas flow to cylinder 164 and eliminating its function. In this situation, the Pop-Off Valve 88 opens and closes as determined by the patient and V/I circuits independent of whether the patient bag is full.

In the operation of the system of FIG. 1, the Selector Valve 124 will be in the position shown for manually assisted and controlled ventilation or spontaneous ventilation. In spontaneous ventilation, fresh gas will continually be supplied via tube 106 to the patient bag 104 and breathing tube 102. Initially expired patient dead space gas will return to the reservoir, i.e., patient bag 104, and then, once bag 104 is full, the patient's alveolar gas will flow through tube 108 through the patient Pop-Off Valve 88 to function as working gas for the V/I subsystem 90. For manually assisted or controlled ventilation, with the Selector Valve 124 in the outside bag position as shown, when the anesthetist squeezes the outside bag 128, the Pop-Off Valve 88 closes, allowing the pressure to increase in the rigid container 118 which is exerted against the walls of the patient bag 104. The settings of the Adjustable Overflow Valve 132 and Biased Check Valve 134 determine the maximum pressure in both the V/I Circuit and the patient circuit. The outside bag 128 provides the anesthetist with essentially the same tactile feedback he would get if he were squeezing the patient bag 104 directly.

If an overpressure condition develops either in the patient or V/I circuit or a gas insufficiency occurs in either circuit, the user can press the flush button 142 to open the Dump Valve 140 and flush the patient circuit, i.e., produce a rapid high flow rate from the high pressure gas source through Flush Valve 143, Check Valve 147 and Needle Valve 148, into the fresh gas line 106. For example, whereas the fresh gas flow via valve 152 is normally less than 10 liters per minute, the flow from Flush Valve 143 to the patient circuit is much greater. This action also flushes the V/I circuit 90 as the high pressure gas overflows through Pop-Off Valve 88, and through the Dump Valve 140 and Biased Check Valve 138. As a consequence, after a flush operation, an initialized pressure condition is established in both the patient and V/I circuit by the bias on Check Valves 134 and 138.

In order to operate in the MECHANICAL VENTILATOR mode, the position of the Selector Valve 124 is changed to disconnect the outside bag 128, and connect the VENTILATOR 126, to the rigid container 118. The MECHANICAL VENTILATOR 126 will then control the pressure on the patient circuit 86 as a consequence of the gas movement past port 123 into and out of the rigid container 118. Overpressurization in the patient and V/I circuits will be avoided by the action of the Biased Check Valve 130 during the expiration phase of the ventilator cycle. An insufficiency of gas volume in the patient and V/I circuits can be immediately rectified by the anesthetist pressing the flush button 142 to Open Valve 143 to flush fresh gas line 106 with high pressure gas.

Figure 3:
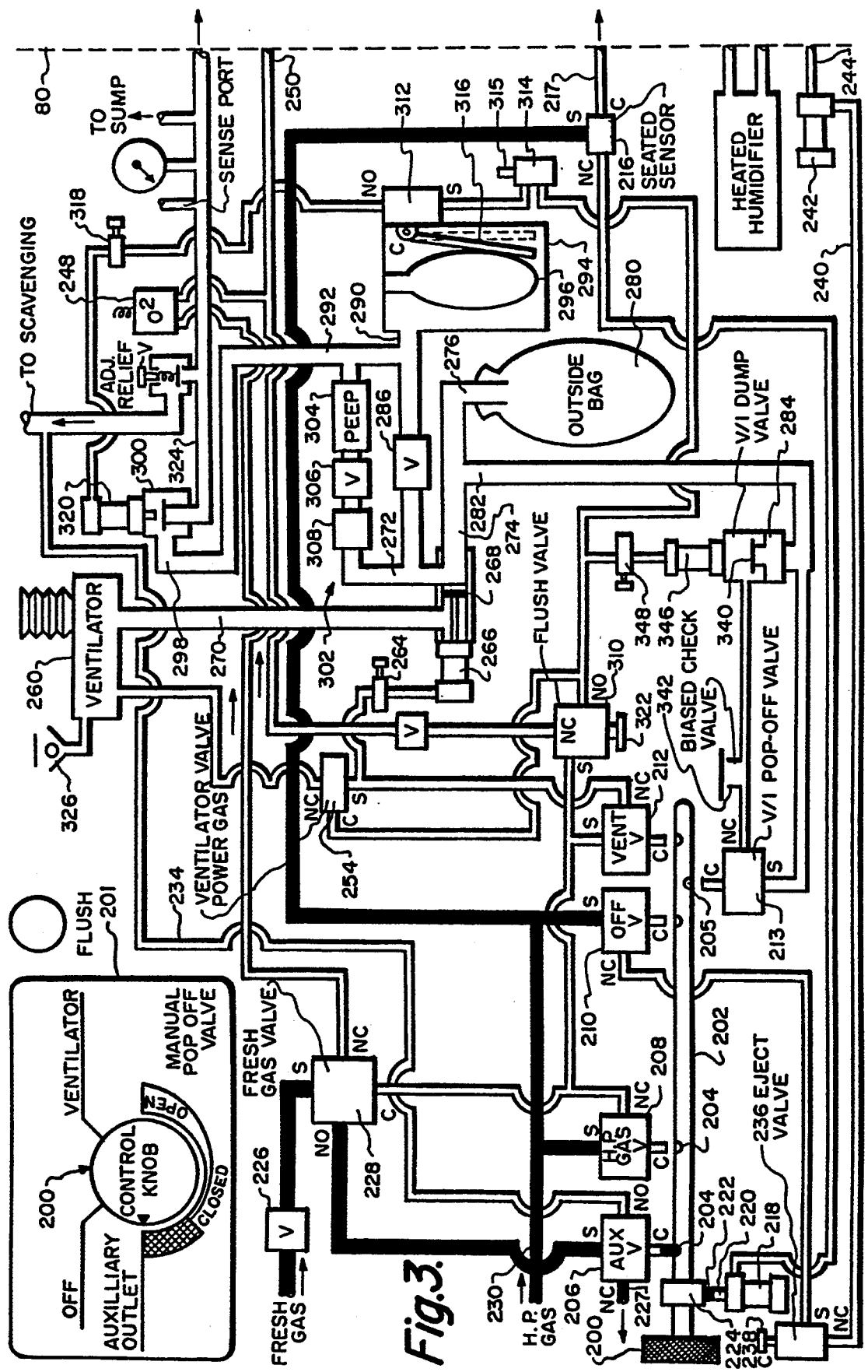
FIG. 3 depicts an implementation of the first embodiment of FIG. 1 in greater detail.

Attention is now directed to FIG. 3 which depicts a preferred implementation of FIG. 1, and which shows a user operable control knob 200 manually rotatable to selectively define each of the different operational modes shown on control panel 201. The control knob 200 is affixed to the end of shaft 202 mounted for rotation about its axis. The control knob and shaft can be implemented as part of a control knob subassembly of the type described in detail in aforementioned U.S. Pat. No. 4,991,576. The shaft 202 carries a plurality of valve actuators, e.g., on-off cams 204, and variable cam 205, each positioned to selectively operate a different valve mounted adjacent to the shaft 202; namely, Auxiliary Fresh Gas Valve 206
High Pressure Gas Valve 208
Off Valve 210
Ventilator Valve 212
V/I Pop-off Valve 213.

These cam operated valves are activated at different rotational positions of the control knob 200 as it moves between the four operating mode positions depicted on control panel 201 in FIG. 3; namely

1. AUXILIARY OUTLET
2. OFF
3. VENTILATOR
4. MANUAL POP-OFF VALVE.

Table I (partitioned for convenience into IA and IB) set forth hereinafter describes the action of each of the aforementioned cam operated valves, as well as various other valves, for each different operating mode, i.e. control knob position.

TABLE IA

VALVE & CYLINDER OPERATION

| NAME | ACTION | CONTROL KNOB POSITION DETACH. CT. SEATED FLUSH BUTTON DEPRESSED | AUXILIARY OUTLET (1) No | AUXILIARY OUTLET (2) Adult | OFF (3) Adult | OFF (4) Adult | VENTILATOR (5) Adult | VENTILATOR (6) Adult * |
|---|---|---|---|---|---|---|---|---|
| Seated Sensor Valve | When Detach. Ct. is seated, high pressure gas goes to Lockpin Cylinder to withdraw pin. | | | * | * | * | * | * |
| Lockpin Cylinder | Lockpin In restricts Control Knob to Auxiliary Outlet and Off Positions. | | In (Locked) | Out | Out | Out | Out | Out |
| Off Valve | Sends high pressure gas to Detach. Ct. Eject Button | | * | * | * | * | | |
| Elect Button | Sends high pressure gas to Eject Cylinder. | | | | | * | | |
| Eject Cylinder | Unlocks and elects Detach. Ct. | | | | | * | | |
| Auxil. Fresh Gas Valve | NC-Sends Fresh Gas to the Auxiliary Outlet. NO-Sends Fresh Gas to Scavenging. | | Aux. | Aux. | Scav. | Scav. | No Gas Supply | No Gas Supply |
| High Pressure Gas Valve | Sends high pressure gas to the: Ventilator(S), Fresh Gas(C). & Flush(S) Valves. | | | | | | * | * |
| Fresh Gas Valve | NC-Sends Fresh Gas to Patient Ct. NO-Sends Fresh Gas to Auxiliary F.G. Valve(S). | | Aux. | Aux. | Aux. | Aux. | Patient | Patient |
| Flush Valve | NC-Sends high pressure gas to flush Patient Ct. NO-Sends high pressure gas to V/I dump(C), PEEP(S), Ventilator Power Gas(S), Full Bag(S) & Pediatric Sensor(S) Valves. | | No Gas Supply | No Gas Supply | No Gas Supply | No Gas Supply | NO Dump Not In Circuit | NC Dump Not In Circuit |
| Ventilator Valve | Sends high pressure gas to Ventilator Power Gas Valve(S) & to move Selector Valve(C) from Bag to Ventilator Position. | | | | | | * | * |
| Vent. Power Gas Valve | Sends high pressure gas to the Ventilator to power it except during Flush. | | | | | | * | |
| Selector Valve | Connects either Outside Bag or Ventilator to V/I Ct. | | Bag | Bag | Bag | Bag | Ventilator Open | Ventilator Open |
| V/I Pop Off Valve | Vents excess gas from V/I Circuit. Variable - Open to closed. | | Closed | Closed | Closed | Closed | Not In Circuit | Not In Circuit |
| V/I Dump Valve | Vents excess gas from V/I Circuit during Flush & in Auxiliary and Off Positions. | | Open | Open | Open | Open | Closed | Open |
| Full Patient Bag Sensor Valve | Senses when Patient Bag is full. Allows Padent Pop Off Valve to open when patient bag is full. | | No Gas Supply | No Gas Supply | No Gas Supply | No Gas Supply | Patent Pop Off Closed | No Gas Supply |
| Pediatric Sensor Valve | Detects when a Pediatric Circuit is seated and inactivates The Full Patient Bag Sensor Subsystem. | | No G Supply | No Gas Supply | No Gas Supply | No Gas Supply | | No Gas Supply |

TABLE IB

VALVE & CYLINDER OPERATION

| NAME | ACTION | CONTROL KNOB POSITION DETACH. CT. SEATED FLUSH BUTTON DEPRESSED | MANUAL POP OFF VALVE | | | |
|---|---|---|---|---|---|---|
| | | | (7) Adult | (8) Adult | (9) Adult * | (10) Pediatric |
| Seated Sensor Valve | When Detach. Ct. is seated, high pressure gas goes to Lockipin Cylinder to withdraw pin. | | * | * | * | * |
| Lockpin Cylinder | Lockpin In restricts Control Knob to Auxiliary Outlet and Off Positions. | | Out | Out | Out | Out |
| Off Valve | Sends high pressure gas to Detach. Ct. Elect Button | | | | | |
| Eject Button | Sends high pressure gas to Eject Cylinder. | | | | | |
| Eject Cylinder | Unlocks and e'ects Detach. Ct. | | | | | |
| Auxil. Fresh Gas Valve | NC-Sends Fresh Gas to the Auxiliary Outlet. NO-Sends Fresh Gas to Scavenging. | | No Gas Supply | No Gas Supply | No Gas Supply | No Gas Supply |
| High Pressure Gas Valve | Sends high pressure gas to the: Ventilator(S), Fresh Gas(C), & Flush(S) Valves. | | * | * | * | * |
| Fresh Gas Valve | NC-Sends Fresh Gas to Patient Ct. NO-Sends Fresh Gas to Auxiliary F.G. Valve(S). | | Patient | Patient | Patient | Patient |
| Flush Valve | NC-Sends high pressure gas to flush Patient Ct. NO-Sends high pressure gas to V/I dump(C), PEEP(S), Ventilator Power Gas(S), Full Bag(S) & Pediatric Sensor(S) Valves. | | NO | NO | NC | NO |
| Ventilator Valve | Sends high pressure gas to Ventilator Power Gas Valve(S) & to move Selector Valve(C) from Bag to Ventilator Position. | | | | | |
| Vent. Power Gas Valve | Sends high pressure gas to the Ventilator to power it except during Flush. | | | | | |
| Selector Valve | Connects either Outside Bag or Ventilator to V/I Ct. | | Bag | Bag | Bag | Bag |
| V/I Pop Off Valve | Vents excess gas from V/I Circuit. Variable - Open to closed. | | Variable Closed | Variable Closed | Variable Open | Variable Closed |
| V/I Dump Valve | Vents excess gas from V/I Circuit during Flushing & in Auxiliary and Off Positions. | | Patient | Patient | No Gas | No Gas |
| Full Patient Bag Sensor Valve | Senses when Patient Bag is full. Allows Patient Pop Off Valve to open when patient bag is full. | | Pop Off Closed | Pop Off Can Open | Supply | Supply |
| Pediatric Sensor Valve | Detects when a Pediatric Circuit is seated and inactivates The Full Patient Bag Sensor Subsystem. | | | | No Gas Supply | * |

To facilitate an understanding of Table I, FIG. 3 specifically depicts the gas flow for exemplary column 1 of Table I which represents the AUXILIARY OUTLET position with no detachable patient circuit seated. In the absence of a seated detachable patient circuit, the NC port of Seated Sensor Valve 216, having a sensor pin 217, remains closed so that no gas is provided to lock pin cylinder 218. Consequently, lock pin 220 remains engaged with slot 222 in flange 224 on shaft 202. This engagement prevents the control knob 200 from rotating to the VENTILATOR and MANUAL POP-OFF positions until a detachable patient circuit is seated. With the control knob in the AUXILIARY OUTLET position and with no detachable circuit seated fresh gas from an attached anesthesia machine (not shown) flows through Check Valve 226 to the S port of Fresh Gas Valve 228. Inasmuch as Fresh Gas Valve 228 is not actuated, the fresh gas supplied thereto is directed out of its NO port to the S port of Auxiliary Fresh Gas Valve 206 and out of its NC port to an Auxiliary Gas Outlet 227 available to the user. High pressure gas is supplied from a source, not shown, via port 230, to the S ports of High Pressure Gas Valve 208, OFF VALVE 210, and Seated Sensor Valve 216. However, none of these valves are active in the state represented in Table I, column 1.

Table I, column 2 shows the control knob still in the AUXILIARY OUTLET position, but with an adult patient circuit seated. This causes the high pressure gas supplied to the S port of Seated Sensor Valve 216 to flow from its NC port to the lock pin cylinder 218 to withdraw lock pin 220 from slot 222.

With the control knob in the OFF position (Table I, column 3) and with an adult patient circuit seated, the Auxiliary Fresh Gas Valve 206 is no longer actuated so that the fresh gas supplied to its S port is now directed to its NO port and then to scavenging via tube 234. Also, in this state, the OFF VALVE 210 is cam actuated so that the high pressure gas supplied to its S port is directed via its NC port to the S port of Eject Valve 236.

Table I, column 4 differs from column 3 in that it assumes that Eject button 238 has been pressed to actuate Eject Valve 236 to direct the high pressure gas supplied to its S port, via its NC port and tube 240 to Eject cylinder 242. Eject cylinder 242 controls Eject pin 244 to unlatch and eject the detachable patient circuit portion, in the manner described in said U.S. Pat. No. 4,991,576.

Table I, column 5 describes the operation when the control knob is in the VENTILATOR position with an adult patient circuit in place. In this state, the High Pressure Gas Valve 208 is cam actuated so that high pressure gas supplied to its S port is directed to its NC port to thus actuate Fresh Gas Valve 228 and direct fresh gas out of its NC port, past oxygen sensor 248 and to the fresh gas interface port 250 (corresponding to port 105 of FIG. 1) for supplying the patient circuit. The NC port of High Pressure Gas Valve 208 also supplies high pressure gas to the S port of cam actuated Ventilator Valve 212 which directs high pressure gas out of its NC port to the S port of the Ventilator Power Gas Valve 254 and via its NC port to the MECHANICAL VENTILATOR 260. Additionally, the high pressure gas flow out of the NC port of Ventilator Valve 212 is supplied past Needle Valve 264 to actuate Selector Valve Cylinder 266 which moves Selector Valve Element 268 to the right (as viewed in FIG. 3), thereby communicating the ventilator output tube 270 with port 272 and sealing port 274. Since port 274 communicates with the entrance 276 to outside bag 280 and with port 282 leading to V/I Dump Valve 284 and the aforementioned cam operated V/I Pop-Off Valve 213, these devices are essentially eliminated from the system during operation in the VENTILATOR mode. In this mode, the ventilator tube 270 communicates via port 272 and check Valve 286 with port 290. Port 290 opens into rigid container 294, which removably accommodates patient bag 296, and via port 292 communicates with outlet 298 of Patient Pop-Off Valve 300. A branch 302 containing Peep Valve 304, Check Valve 306, and spirometer 308 couples port 292 back to port 272.

Note also that in the VENTILATOR operating mode (Table I, column 5), the High Pressure Gas Valve 208 NC port supplies the S port of Flush Valve 310 whose NO port supplies the S port of the Full Patient Bag Sensor Valve 312, via the Pediatric Circuit Sensor Valve 314. As will be discussed hereinafter, the Valve 314 is actuated when a pediatric patient circuit is seated to depress pin 315. When an adult patient circuit is seated, Valve 314 is not actuated and gas supplied to its S port is directed via its NO port to the S port of the Full Patient Bag Sensor Valve 312. The Valve 312 is actuated by the Full Bag Sensor lever 316 mounted in rigid container 294 when the patient bag 296 is full. When the patient bag is less than full, the lever 316 is biased to its clockwise position depicted in FIG. 3, allowing the NO port of Valve 312 to supply gas via Needle Valve 318 to cylinder 320 to hold the Patient Pop-Off Valve 300 closed to prevent patient gas overflow from tube 324. However, when the patient bag 298 becomes sufficiently full to physically move the lever 316 to the dashed counter clockwise position depicted in FIG. 3, it actuates Valve 312 to cut off the gas supply to cylinder 320. With the supply cut off to cylinder 320, the Patient Pop-Off Valve 300 is allowed to open permitting patient gas to overflow via port 298, providing working gas to the V/I circuit.

Table I, column 6 represents the VENTILATOR position of column 5 when the Flush button 322 controlling Flush Valve 310 is pressed. When this occurs, the gas previously directed to the NO port of Flush Valve 310 is cut off and instead directed out of its NC port past Check Valve 324 into the patient circuit via the oxygen sensor 248 and fresh gas interface port 250. This high pressure gas will flood the patient circuit and via the patient Pop-Off Valve 300 and port 298 will flush the V/I circuit. The action will thereby initialize pressure and volume in both the patient and V/I circuits as determined by the bias on the Ventilator Check Valve 326.

Columns 7, 8 and 9 of Table I describe the operation of the V/I circuit with the control knob 200 in the MANUAL POP-OFF VALVE position and with a detachable adult circuit in place. Column 7 relates to the condition when the patient bag is not full and the cylinder 320 is holding the Patient Pop-Off Valve 300 closed. Column 8 relates to the condition when the patient bag is full thereby actuating the Full Bag Sensor Valve 312 to cut off the supply to cylinder 320 and permit the patient Pop-Off Valve 300 to open. Column 9 describes the operation when the flush button 320 is pressed.

With the control knob 200 in the MANUAL POP-OFF VALVE position (Table I, columns 7–10), the VENTILATOR VALVE 212 is no longer actuated.

Thus, cylinder 266 is not actuated and the valve element 268 moves to the position depicted in FIG. 3. This action removes the MECHANICAL VENTILATOR 260 from the system and couples aforementioned ports 272 and 274, thus coupling the outside bag 280, via Check Valve 286, to the entrance 290 to the rigid container 294.

The outside bag 280 is also coupled via port 282 to the supply inputs of V/I Dump Valve 284 and V/I Pop-Off Valve 213. The V/I Dump Valve 284 comprises a Check Valve including valve element 340. The outlet of Dump Valve 284 supplies a Biased Check Valve 342 whose output is coupled to scavenging. The NC port of V/I Pop-Off Valve 213 is also coupled to the Biased Check Valve 342. The NO port of Flush Valve 310 is coupled to cylinder 346 via a Needle Valve 348. The cylinder 346 is mounted adjacent to the valve element 340 of Dump Valve 284. When the cylinder 346 is powered, it holds the Dump Valve 284 closed. This is the condition represented in Table I, column 7.

The V/I Pop-Off Valve 213 is a variable orifice valve controlled by variable cam 205 mounted on shaft 202. Rotation of the shaft 202 in the MANUAL POP-OFF VALVE position varies the orifice of the Valve 213 between full closed and full open as represented on the control panel 201 shown in FIG. 3.

In the state represented by Table I, column 7, the High Pressure Gas Valve 208 is still actuated supplying high pressure gas to the Flush Valve 310. The Flush Valve NO port then supplies high pressure gas via the Pediatric Circuit Sensor Valve 314 to the Full Bag Sensor Valve 312. With the patient bag 296 less than full, the Patient Pop-Off Valve 300 is held closed, via the cylinder 320, as previously described in connection with the operation represented by Table I, column 5. In use, the anesthetist rotates the control knob 200 to set the orifice of the V/I Pop-Off Valve 213. The anesthetist then squeezes the outside bag 280 to control or assist patient ventilation. More specifically, as the outside bag 280 is squeezed, gas is transferred therefrom via Check Valve 286 to the rigid container exerting pressure against patient bag 296. Gas flow out of the rigid container 294 returns to the outside bag 280 via branch 302.

Table I, column 8 describes the condition when a patient bag 219 fills sufficiently to actuate Full Bag Sensor Valve 312. This action cuts off the gas supply to cylinder 320 and permits the Patient Pop-Off Valve 300 to open. This allows patient gas to overflow via tube 324 into the V/I circuit when the patient circuit pressure exceeds the bias on Valve 300.

Table I, column 9 summarizes the operation when the flush button 320 is pressed. As was described in connection with Table I, column 6, high pressure gas is supplied by the NC port of Flush Valve 310 to the patient circuit via interface port 250, flushing the patient circuit and supplying gas via the Patient Pop-Off Valve 300 to the V/I circuit. In response to the flush button 320 being pressed, the supply gas to cylinder 346 is cut off thus allowing the Dump Valve 284 to open to permit gas flow to scavenging via Biased Check Valve 342. The bias on Check Valve 342 thus sets the initialized gas pressure and volume in the V/I circuit after the flush button is released and operation resumed.

Table I, column 10 describes the condition when the control knob 200 is in the MANUAL POP-OFF VALVE position and a pediatric breathing circuit is seated instead of an adult breathing circuit. Column 10 is identical to column 7 except that it shows that the Pediatric Circuit Sensor Valve 314 is actuated. This cuts off the gas supply to the Full Patient Bag Sensor 312 and thus, the Patient Pop-Off Valve 300 is permitted to open to pass patient overflow gas. System operation is substantially identical to that described in connection with column 8.

Attention is now directed to FIG. 2 which comprises a block diagram of a second system embodiment in accordance with the present invention. The detachable portion 82 of FIG. 2 is identical to that shown in FIG. 1 and communicates across interface 80' with a permanent portion 84'. The permanent portion 84' differs from the permanent portion 84 of FIG. 1 primarily as a consequence of the V/I circuit 90' using supplemental gas, e.g., dry medical grade oxygen, for working gas (i.e. to fill the rigid container, outside bag and associated tubing) whereas the V/I circuit 90 of FIG. 1 used patient circuit gas from the overflow tube 108 as V/I working gas. The use of patient circuit gas as working gas does not present a cross contamination risk inasmuch as gas flow though the overflow tube 108 can occur in only one direction past the Patient Pop-Off Valve 88 and there is no path in FIG. 1 for the V/I working gas to reenter the patient circuit. However, the disadvantage of using patient expired gas for V/I circuit working gas is that it is generally of high humidity and may have impurities, such as blood or phlegm which could, over extended periods, affect the reliability of valving and flow in the V/I circuit as well as the MECHANICAL VENTILATOR. Although this risk is minimal if the permanent portion is properly maintained, the system of FIG. 2 avoids this possibility by using a high pressure gas supply to provide working gas.

Thus, it will be noted that the system of FIG. 2 differs from that of FIG. 1 in that instead of using a Check Valve as the Patient Pop-Off Valve 88, FIG. 2 uses a Balanced Valve 350 for this purpose. Valve 350 includes valve element 351 which will either be seated to Close Valve 350 entirely or open to permit gas flow from overflow tube 108 to scavenging via port 352. FIG. 2 further differs in that Flush Valve 353 operable by Flush button 354, is coupled to an additional port 355, via Check Valve 356 and Needle Valve 358, communicating with both the upper chamber 360 of the Balanced Pop-Off Valve 350 and the entrance 361 to the rigid container 362. The outlet 352 of Pop-Off Valve 350 is coupled through a PEEP Valve 366 to scavenging. The PEEP Valve 366 in the Patient Pop-Off Valve flow path serves to maintain a substantially constant PEEP (positive end expiratory pressure) level against which a patient exhales, even after the Pop-Off Valve 350 opens.

Operation of the system of FIG. 2 is similar to that described for FIG. 1 except it should be noted that when the Flush button 354 is pressed, with the Selector Valve in the outside bag position, not only will high pressure gas be supplied to the fresh gas line 370, via Check Valve 371, for flushing the patient circuit, but in addition high pressure gas will be supplied via port 355 to the V/I circuit including rigid container 362 and outside bag 374. At this time, inasmuch as the pressing of the Flush button 354 allows Dump Valve 376 to open, the gas volume in the V/I circuit will either increase (as a consequence of flow into port 355) or decrease (as a consequence of outflow past Dump Valve 376 and Check Valve 377. At the conclusion of the flush operation, the initialized gas volume and pressure in the V/I circuit will be determined primarily by the bias on Check Valve 377. When the Flush button 354 is pressed with the Selector Valve in the VENTILATOR position, the high pressure gas from the Flush Valve 353 NC port, in addition to being supplied to fresh gas line 370 via Check Valve 371, will be supplied via port 355 to the VENTILATOR 382 to fill its bellows. In this case, the Biased Ventilator Check Valve 384, rather than Check Valve 377, will determine the initialized gas volume and pressure in the V/I circuit after a flush operation. As in FIG. 1, a cylinder 388 is mounted adjacent to the Patient Pop-Off Valve 350 to hold the valve closed until the patient bag 386 is full to maximize efficient use of the fresh gas.

It should also be noted in the systems of both FIGS. 1 and 2 that even when the patient bag is full, thus releasing hold down cylinders 164, 388, flow through the patient overflow tube 108 does not occur during inspiration. That is, on inspiration, the Patient Pop-Off Valves are always closed. Therefore the system can preferentially vent alveolar gas and preserve dead space and fresh gas to enhance efficiency.

Figure 4:
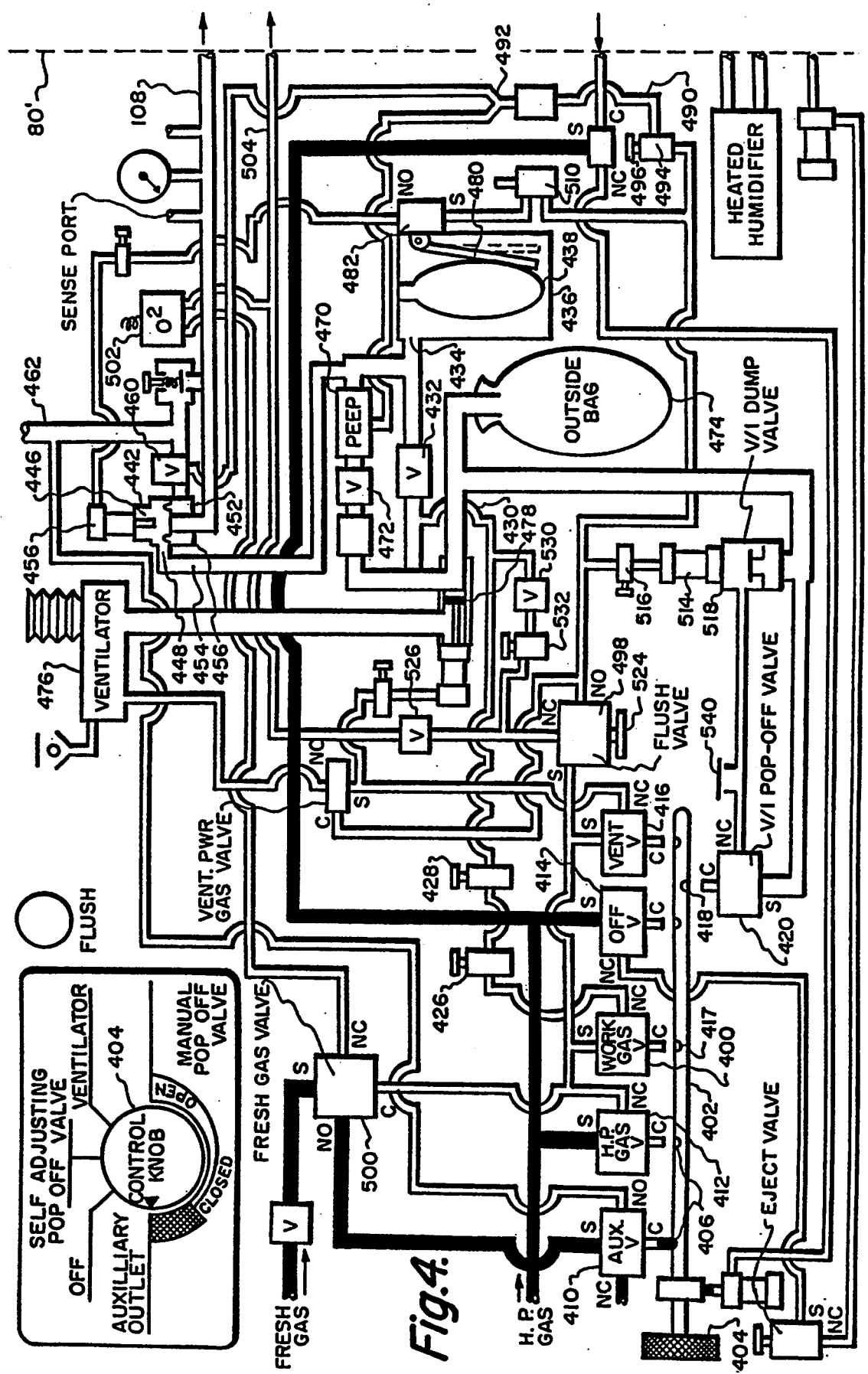
FIG. 4 depicts an implementation of the second embodiment of FIG. 2 in greater detail.

Attention is now directed to FIG. 4 which shows a preferred implementation of the second embodiment of FIG. 2. The implementation of FIG. 4 is similar to that described in FIG. 3 except in certain significant respects which will be discussed first. Initially, note that an additional cam operated valve, i.e., Working Gas Valve 400, is mounted adjacent to shaft 402 connected to control knob 404. As in FIG. 3, the shaft 402 carries a plurality of on-off cams 406 which function to actuate a different one of the aforementioned cam operated valves i.e., Auxiliary Valve 410, the High Pressure Gas Valve 412, the OFF VALVE 414, and the Ventilator Valve 416. An additional on-off cam 417 is provided to actuate the Working Gas Valve 400 when the control knob is in the Ventilator and MANUAL POP-OFF VALVE positions. As was discussed in connection with FIG. 3, variable cam 418 differs from the other cams in that it variably opens the orifice on the V/I Pop-Off Valve 420.

The NC port of the Working Gas Valve 400 is connected via Needle Valves 426 and 428 to port 430. Check Valve 432 connects port 430 to the entrance 434 of rigid container 436 accommodating patient bag 438.

An additional difference between FIGS. 4 and FIG. 3 should be noted by reference to the control panel 440. Note that an additional operating mode is defined between the OFF and the VENTILATOR position; namely, a SELF ADJUSTING POP-OFF VALVE mode. The system operation in this mode will be discussed hereinafter in connection with Table II.

A still further feature distinguishing FIG. 4 from FIG. 3 has been mentioned in connection with FIG. 2. More particularly, note that the patient overflow tube 108 is coupled to a biased balanced Pop-Off Valve 442 including valve element 446. As is characteristic of balanced valves, the element 446 separates upper and lower chambers 448, 450. When the pressure in the upper chamber 448 equals or exceeds that in the lower chamber 450, the valve element 446 will be seated thus preventing overflow from the overflow tube 108. When the pressure in the lower chamber 450 exceeds that in the upper chamber 448, then the valve element is unseated allowing overflow from tube 108 to outlet 452. The pressure in the upper chamber 448 is controlled by the V/I circuit applying pressure to port 454. In accordance with the present invention, and in a manner similar to that described in connection with FIG. 3, a hold down cylinder 456 is provided for holding the valve element 446 seated to prevent overflow from tube 108 whenever the patient bag 438 is not full. This operation will be discussed further in connection with Table II hereinafter.

Figure 5:
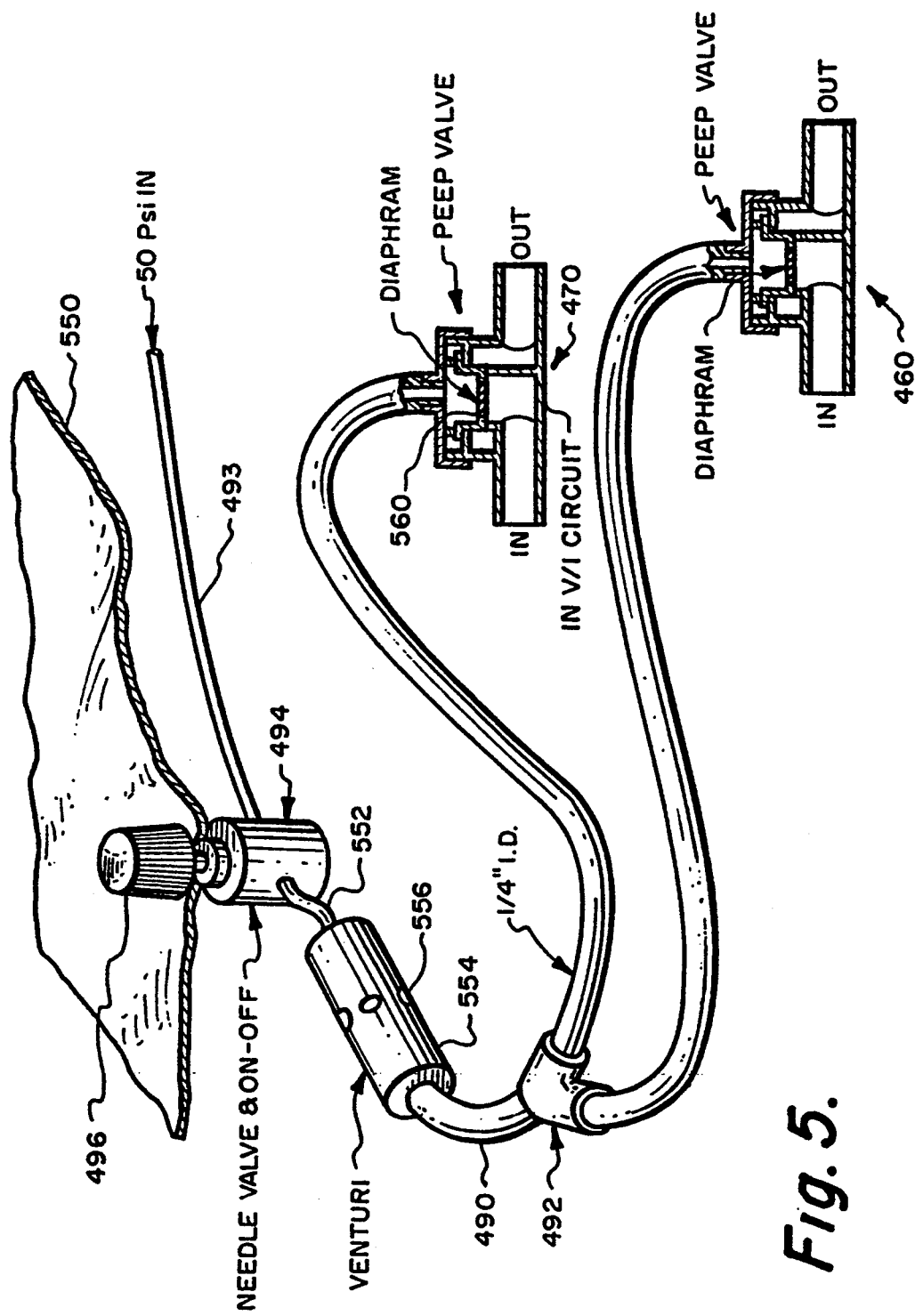
FIG. 5 is an isometric schematic representation of the PEEP subsystem used in the second system embodiment of FIG. 4.
Figure 6:
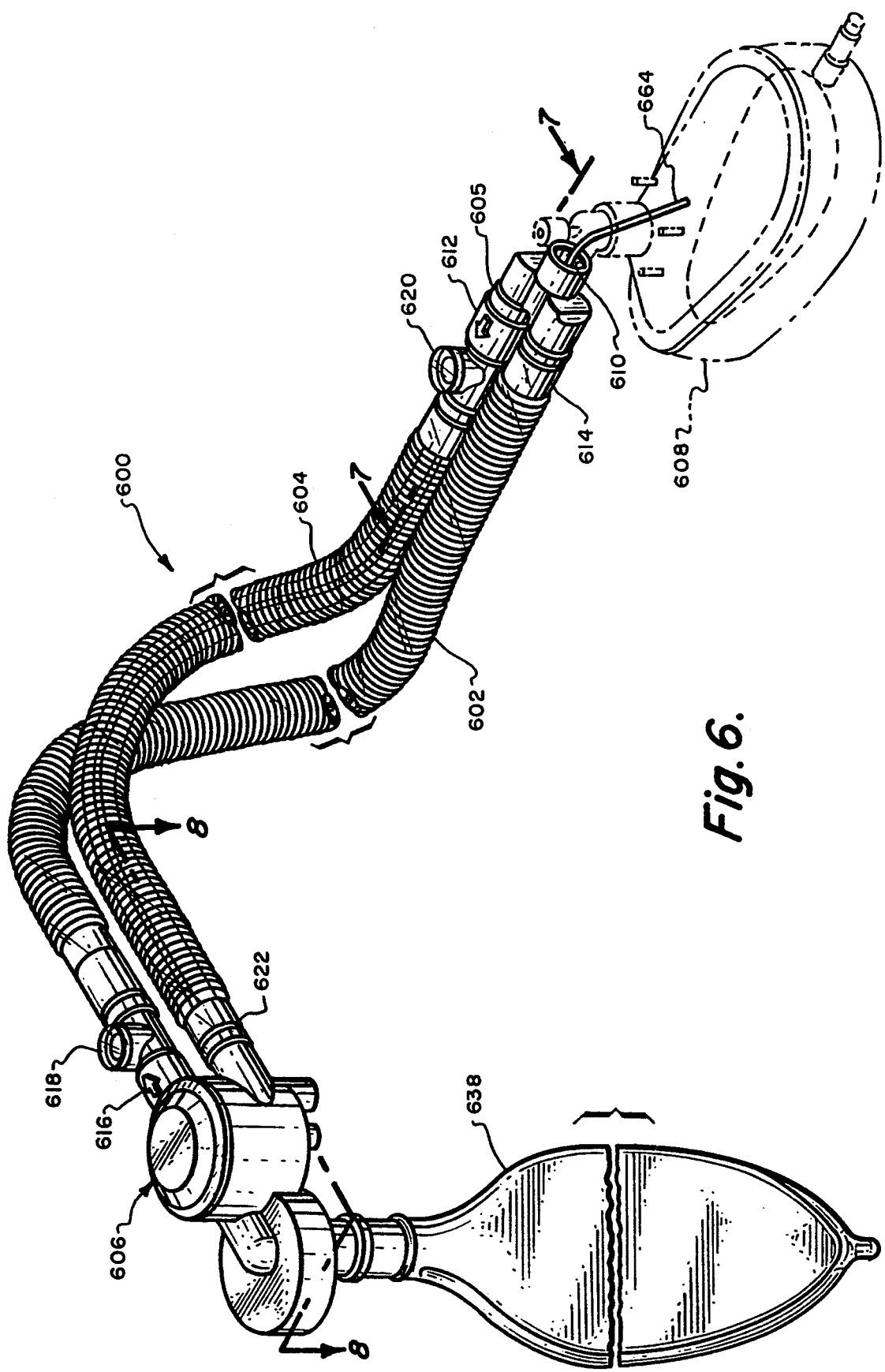
FIG. 6 is an isometric illustration of a preferred detachable portion implementing the patient circuit represented in FIGS. 1 and 2.

A PEEP valve 460 is connected in the patient overflow path between the Pop-Off Valve Outlet 452 and a scavenging manifold 462. The PEEP Valve 460 supplements a PEEP Valve 470 communicating with the entrance 434 of rigid container 436. The purpose of the PEEP Valve 470 is to establish a positive end expiratory pressure against which the patient breaths. Thus, as the patient exhales into the patient bag 438, gas in the rigid container will be displaced via the PEEP Valve 470 and Check Valve 472 either to the outside bag 474 or VENTILATOR 476 depending upon the position of the Selector Valve 478. During the time that the patient bag 438 is not full, the cylinder 456 associated with the Patient Pop-Off Valve element 446 will be actuated to hold down the element 446 thus maintaining the patient overflow path closed. With the valve element 446 sealing the patient overflow path, it is the PEEP Valve 470 which primarily establishes the pressure level against which the patient exhales. Once the patient bag 438 is full, it will engage lever 480 to actuate Full Bag Sensor Valve 482 to cut off the gas supplied to cylinder 456. This action permits the unseating of valve element 446 and essentially removes the PEEP Valve 470 as the pressure determining element against which the patient exhales. However, the overflow path from tube 108 and Pop-Off Valve Outlet 452 is through PEEP Valve 460 which takes over the job of establishing the PEEP level after the patient bag 438 fills. Preferably, the PEEP Valves 470 and 460 are set to the same value. As depicted in FIGS. 4 and 5, this is accomplished by deriving control lines for both PEEP Valves from a common supply line 490 upstream from a Y junction 492. Gas is supplied to the Y junction 490 via a Needle Valve 494 whose knob 496 enables a user to selectively establish the PEEP level in both PEEP Valves 470 and 460. High pressure gas is supplied to the PEEP Control Valve 494 from the NO port of Flush Valve 498.

Attention is now directed to Table II which describes the operation of the implementation of FIG. 4. Inasmuch as the operation of the implementations of FIGS. 3 and 4 is substantially identical in the AUXILIARY OUTLET and OFF operational modes, Table II, columns 1–4 are substantially the same as columns 1–4 of Table I. Similarly, columns 8–13 of Table II are substantially identical to columns 5–10 of Table I describing the VENTILATOR and MANUAL POP-OFF VALVE operational modes for the respective implementations. Do recall however that whereas the V/I working gas in FIG. 3 is derived from the Patient Pop-Off Valve 300, in the implementation of FIG. 4 the V/I working gas is supplied from the NC port of the Working Gas Valve 400 via port 430. Columns 5, 6 and 7 of Table II describe the operation in the SELF ADJUSTING POP-OFF VALVE mode shown on the control panel 440 of FIG. 4. This operation mode does not have a counterpart in Table I and will be described in more detail hereinafter.

TABLE IIA

VALVE & CYLINDER OPERATION

| NAME | ACTION | CONTROL KNOB POSITION DETACH. CT. SEATED FLUSH BUTTON DEPRESSED | AUXILIARY OUTLET | | OFF | |
|---|---|---|---|---|---|---|
| | | | (1) No | (2) Adult | (3) Adult | (4) Adult |
| Seated Sensor Valve | When Detach. Ct. is seated, high pressure gas goes to Lockpin Cylinder to withdraw pin. | | | * | * | * |
| Lockpin Cylinder | Lockpin In restricts Control Knob to Auxiliary Outlet and Off Positions. | | In (Locked) | Out | Out | Out |
| Off Valve | Sends high pressure gas to Detach. Ct. Elect Button | | * | * | * | * |
| Eject Button | Sends high pressure gas to Eject Cylinder. | | | | | * |
| Eject Cylinder | Unlocks and ejects Detach. Ct. | | | | | * |
| Auxil. Fresh Gas Valve | NC-Sends Fresh Gas to the Auxiliary Outlet. NO-Sends Fresh Gas to Scavenging. | | Aux. | Aux. | Scav. | Scav. |
| High Pressure Gas Valve | Sends high pressure gas to the: Ventilator(S), Fresh Gas(C), & Flush(S) Valves. | | | | | |
| Fresh Gas Valve | NC-Sends Fresh Gas to Patient Ct. NO-Sends Fresh Gas to Auxiliary F.G. Valve(S). | | Aux. | Aux. | Aux. | Aux. |
| Working Gas Valve | Sends Working (High Pressure) Gas to V/I Circuit. | | | | | |
| Flush Valve | NC-Sends high pressure gas to flush Patient Circuit & V/I Circuit. | | No Gas Supply | No Gas Supply | No Gas Supply | No Gas Supply |
| | NO-Sends high pressure gas to V/I dump(C), PEEP(S), Ventilator Power Gas(S), Full Bag(S) & Pediatric Sensor(S) Valves. | | | | | |
| Ventilator Valve | Sends high pressure gas to Ventilator Power Gas Valve(S) & to move Selector Valve(C) from Bag to Ventilator Position. | | | | | |
| Vent. Power Gas Valve | Sends high pressure gas to the Ventilator to power it except during Flush. | | | | | |
| Selector Valve | Connects either Outside Bag or Ventilator to V/I Ct. | | Bag | Bag | Bag | Bag |
| V/I Pop Off Valve | Vents excess gas from V/I Circuit. Variable - Open to closed. | | Closed | Closed | Closed | Closed |
| V/I Dump Valve | Vents excess gas from V/I Circuit during Flush & in Auxiliary and Off Positions. | | Open | Open | Open | Open |
| Full Patient Bag Sensor Valve | Senses when Patient Bag is full. Allows Patient Pop Off Valve to open when patient bag is full. | | No Gas Supply | No Gas Supply | No Gas Supply | No Gas Supply |
| Pediatric Sensor Valve | Detects when a Pediatric Circuit is seated and inactivates The Full Patient Bag Sensor Subsystem. | | No Gas Supply | No Gas Supply | No Gas Supply | No Gas Supply |

SELF-ADJUSTING

TABLE IIA-continued
VALVE & CYLINDER OPERATION

| NAME | ACTION | CONTROL KNOB POSITION DETACH. CT. SEATED FLUSH BUTTON DEPRESSED | POP OFF VALVE | | |
|---|---|---|---|---|---|
| | | | (5) Adult | (6) Adult | (7) Adult * |
| Seated Sensor Valve | When Detach. Ct. is seated, high pressure gas goes to Lockpin Cylinder to withdraw pin. | | * | * | * |
| Lockpin Cylinder | Lockpin In restricts Control Knob to Auxiliary Outlet and Off Positions. | | Out | Out | Out |
| Off Valve | Sends high pressure gas to Detach. Ct. Elect Button | | | | |
| Eject Button | Sends high pressure gas to Eject Cylinder. | | | | |
| Eject Cylinder | Unlocks and ejects Detach. Ct. | | | | |
| Auxil. Fresh Gas Valve | NC-Sends Fresh Gas to the Auxiliary Outlet. NO-Sends Fresh Gas to Scavenging. | | No Gas Supply | No Gas Supply | No Gas Supply |
| High Pressure Gas Valve | Sends high pressure gas to the: Ventilator(S), Fresh Gas(C), & Flush(S) Valves. | | * | * | * |
| Fresh Gas Valve | NC-Sends Fresh Gas to Patient Ct. NO-Sends Fresh Gas to Auxiliary F.G. Valve(S). | | Patient | Patient | Patient |
| Working Gas Valve | Sends Working (High Pressure) Gas to V/I Circuit. | | | | |
| Flush Valve | NC-Sends high pressure gas to flush Patient Circuit & V/I Circuit. NO-Sends high pressure gas to V/I dump(C), PEEP(S), Ventilator Power Gas(S), Full Bag(S) & Pediatric Sensor(S) Valves. | | NO | NO | NC |
| Ventilator Valve | Sends high pressure gas to Ventilator Power Gas Valve(S) & to move Selector Valve(C) from Bag to Ventilator Position. | | | | |
| Vent. Power Gas Valve | Sends high pressure gas to the Ventilator to power it except during Flush. | | | | |
| Selector Valve | Connects either Outside Bag or Ventilator to V/I Ct. | | Bag | Bag | Bag |
| V/I Pop Off Valve | Vents excess gas from V/I Circuit. Variable - Open to closed. | | Closed | Closed | Closed |
| V/I Dump Valve | Vents excess gas from V/I Circuit during Flush & in Auxiliary and Off Positions. | | Closed | Closed | Open |
| Full Patient Bag Sensor Valve | Senses when Patient Bag is full. Allows Patient Pop Off Valve to open when patient bag is full. | | Patient Pop Off Closed | Patient Pop Off Can Open | No Gas Supply |
| Pediatric Sensor Valve | Detects when a Pediatric Circuit is seated and inactivates The Full Patient Bag Sensor Subsystem. | | | | No Gas Supply |

TABLE IIB
VALVE & CYLINDER OPERATION

| NAME | ACTION | CONTROL KNOB POSITION DETACH. CT SEATED FLUSH BUTTON DEPRESSED | VENTILATOR | | MANUAL POP OFF VALVE | | | |
|---|---|---|---|---|---|---|---|---|
| | | | (8) Adult | (9) Adult * | (10) Adult | (11) Adult | (12) Adult * | (13) Pediatric |
| Seated Sensor Valve | When Detach. Ct. is seated, high pressure gas goes to Lockpin Cylinder to withdraw pin. | | * | * | * | * | * | * |
| Lockpin Cylinder | Lockpin In restricts Control Knob to Auxiliary Outlet and Off Positions. | | Out | Out | Out | Out | Out | Out |
| Off Valve | Sends high pressure gas to Detach. Ct. Eject Button | | | | | | | |
| Eject Button | Sends high pressure gas to Eject Cylinder. | | | | | | | |
| Eject Cylinder | Unlocks and ejects Detach. Ct. | | | | | | | |
| Auxil. Fresh Gas Valve | NC-Sends Fresh Gas to the Auxiliary Outlet. NO-Sends Fresh Gas to Scavenging. | | No Gas Supply | No Gas Supply | No Gas Supply | No Gas Supply | No Gas Supply | No Gas Supply |
| High Pressure Gas Valve | Sends high pressure gas to the: Ventilator(S), Fresh Gas(C). & Flush(S) Valves. | | * | * | * | * | * | * |
| Fresh Gas Valve | NC-Sends Fresh Gas to Patient Ct. NO-Sends Fresh Gas to Auxiliary F.G. Valve(S). | | Patient | Patient | Patient | Patient | Patient | Patient |
| Working Gas Valve | Sends Working (High Pressure) Gas to V/I Circuit. | | * | * | * | * | * | * |
| Flush Valve | NC-Sends high pressure gas to flush Patient Circuit & V/I Circuit. NO-Sends high pressure gas to V/I dump(C), PEEP(S), Ventilator Power Gas(S), Full Bag(S) & Pediatric Sensor(S) Valves. | | NO Dump Not In Circuit | NC Dump Not In Circuit | NO | NO | NC | NO |
| Ventilator Valve | Sends high pressure gas to Venfilator Power Gas Valve(S) & to move Selector Valve(C) from Bag to Ventilator Position. | | * | * | | | | |
| Vent. Power Gas Valve | Sends high pressure gas to the Ventilator to power it except during Flush. | | * | | | | | |
| Selector Valve | Connects either Outside Bag or Ventilator to V/I Ct. | | Ventilator | Ventilator | Bag | Bag | Bag | Bag |
| V/I Pop Off Valve | Vents excess gas from V/I Circuit. Variable - Open to closed. | | Open Not In Circuit | Open Not In Circuit | Variable | Variable | Variable | Variable |
| V/I Dump | Vents excess gas from V/I Circuit during | | Closed | Open | Closed | Closed | Open | Closed |

TABLE IIB-continued

| | | | VALVE & CYLINDER OPERATION | | | | | |
|---|---|---|---|---|---|---|---|---|
| | | | VENTILATOR | | MANUAL POP OFF VALVE | | | |
| NAME | ACTION | CONTROL KNOB POSITION DETACH. CT SEATED FLUSH BUTTON DEPRESSED | (8) Adult | (9) Adult * | (10) Adult | (11) Adult | (12) Adult * | (13) Pediatric |
| Valve | Flushing & in Auxiliary and Off Positions. | | | | | | | |
| Full Patient Bag Sensor Valve | Senses when Patient Bag is full. Allows Patient Pop Off Valve to open when patient bag is full. | | Patient Pop Off Closed | No Gas Supply | Patient Pop Off Closed | Patient Pop Off Can Open | No Gas Supply | No Gas Supply |
| Pediatric Sensor Valve | Detects when a Pediatric Circuit is seated and inactivates The Full Patient Bag Sensor Subsystem. | | | No Gas Supply | | | No Gas Supply | * |

Column 5 assumes that the control knob 404 is in the SELF ADJUSTING POP-OFF VALVE position and that an adult detachable circuit is seated. In this position, the High Pressure Gas Valve 412 is actuated thus supplying gas, via its NC port to the control port of Fresh Gas Valve 500. This actuates Fresh Gas Valve 500 and enables it to supply fresh anesthesia gas via its NC port past oxygen sensor 502 to the fresh gas interface port 504. The gas output from the High Pressure Gas Valve NC port also flows through the Flush Valve 498 to the pediatric circuit detector 510 and then through the Full Bag Sensor Valve 482 to the hold down cylinder 456. Additionally, hold down cylinder 514 is actuated via gas supplied through Check Valve 516 to hold closed the V/I Dump Valve 518. Inasmuch as the V/I Pop-Off Valve 420 is not actuated in the state represented in column 5, the V/I circuit is thus fully sealed. In this operating mode, the anesthetist can squeeze the outside bag 474 to pressurize the rigid container 436 to thus effectively squeeze the patient bag 438. Assuming no system leaks, the squeezing pressure applied to the outside bag 474 is correspondingly transferred to the patient bag 438.

Once the patient bag 438 fills, it will move lever 480 to the dash line position to actuate the Full Bag Sensor Valve 482 to cut off the gas supplied to the hold down cylinder 456, thereby releasing the valve member 446. This situation is represented by Table II, column 6. It is instructive to note that until the Full Bag Sensor Valve is actuated, the patient exhales against a pressure level established by the PEEP Valve 470 exerted against the patient bag. Once the Full Bag Sensor Valve 482 is actuated, patient overflow gas can flow to scavenging via the outlet 452. In accordance with the invention, this overflow path includes the second PEEP Valve 460 which is set to the same pressure level as PEEP Valve 470 as a consequence of the gas supplied via Y junction 492. Thus, the pressure level against which the patient breaths is maintained constant.

With the system operating as represented in Table II, column 6, assume now that flush button 524 is pressed. This action is described by Table II, column 7. When flush button 524 is pressed, gas is no longer available from the NO port of Flush Valve 498. Instead, gas flows out of the Flush Valve NC port via Check Valve 526 to the fresh gas interface port 504, via oxygen sensor 502. This action flushes the patient circuit as gas flows via the overflow tube 108, the Pop-Off Valve 442, and out through the scavenging manifold 462. The hold down cylinder 456 is not active in this state because its gas supply from the NO port of Flush Valve 498 has been cut off. In addition to flushing the patient circuit, the high pressure gas flow from the Flush Valve NC port flows through Needle Valve 530 and Check Valve 532 to port 430. This flow flushes the rigid container and outside bag and exits through the Dump Valve 518 which is no longer held closed inasmuch as the supply to hold down cylinder 514 is cut off by actuation of the Flush Valve 498. After completion of the flush operation the gas pressure and volume in the V/I circuit will be initialized at a level determined by Biased Check Valve 540. The pressure and volume in the patient circuit will be initialized at a level primarily determined by the bias on the Patient Pop-Off Valve 442.

Attention is now directed to FIG. 5 which illustrates a preferred implementation of the two PEEP Valves 460 and 470 utilized in the implementation of FIG. 4. More specifically, note that FIG. 5 depicts the Needle Valve 494 mounted on a structural surface 550 to provide user access to the PEEP control knob 496. As was discussed in FIG. 4, supply gas from the NO port of Flush Valve 498 is supplied via tube 493 to the Needle Valve 494. The output of the Needle Valve 494 is passed through a narrow discharge orifice (not shown) defined by tube 552 into the entrance of a venturi device 554. The high velocity low pressure gas stream introduced into the venturi 554 pulls in outside air via ports 556 to create a static pressure in the venturi outlet. Tube 490 transmits this pressure via Y piece 492 to the PEEP Valves 460 and 470. The gas pressure supplied to PEEP Valves bear against an internal diaphragm 560, movable between open and closed positions, so as to establish a pressure which must be exceeded in order for gas to flow from the PEEP Valve in port to its out port.

Attention is now directed to FIGS. 6, 7, 8, 9A, 9B, 10 which are substantially identical to FIGS. 8–10 and 12–14 of U.S. Pat. No. 4,991,576 and which depict a preferred structural embodiment 500 of the detachable (single use or sterilizable) portion of the patient circuit. More particularly, the detachable patient circuit portion 500 is shown as including first and second corrugated tubes 502 and 504 connected between a Y-piece 505 and a connector body 506. The Y-piece 505 is intended to be connected to a mask elbow fitting and then to a mask 508 or endotracheal tube (not shown). The Y-piece is shown as including ports 510, 512, and 514. Tube 502 extends from a fitting 516 on the connector body through a coupling including Inspiratory Valve 518 and then to the port 514 on Y-piece 505. The tube 504 extends from the port 512 on Y-piece 505 through a coupling including Expiratory Valve 520 to fitting 522 of the connector body 506.

FIG. 8 best shows the structure of connector body 506. Note that it includes two substantially cylindrical structures 530 and 532. When seated on the permanent portion mounting structure (533 in FIGS. 9 and 10), the cylindrical portion 530 caps the rigid container 534 which, it will be recognized, corresponds to the rigid container referred to in FIGS. 1-4. The cap portion 530 includes a depending nipple 536 around which the mouth of the patient bag 538 is secured. For enhanced reliability and lower cost, the bag 538 does to require a cuff but instead can be directly bonded to nipple 536. The patient bag 538 corresponds to the patient bag previously referred to in FIGS. 1-4. Note in FIG. 8 that the nipple 536 communicates via a passageway 540 with the proximal end of inspiratory tube 502.

The cylindrical portion 532 of the connector body 506 defines three depending open nipples 550A, 552A and 554A. Note that nipple 550A communicates with the inspiratory tube 502 via the aforementioned passageway 540.

In accordance with a preferred configuration of the detachable patient circuit 500, the patient overflow tube (e.g., 108 in FIGS. 1 and 2) is threaded through the expiratory tube 504. Thus, as can be seen in FIG. 8, a tube 556 is provided extending the full length of tube 504 from the Expiratory Valve 520 to the connector body 506. More particularly, the Valve 520 (FIG. 7) is housed in fitting 555 having a first tubular end 556, preferably bonded to the Y-piece 505. The proximal end of fitting 555 terminates in spaced concentric nipples 557, 558. The distal end of expiratory tube 504 is preferably bonded to the outer nipple 557 providing a gas passageway from tube 504, through the space between nipples 557 and 558, to the Valve 520. The overflow tube 556 is fitted on and preferably bonded to inner nipple 558.

The proximal end of expiratory tube 504 is fitted around and preferably bonded to nipple 522 on connector body 506. An inner nipple 560 is concentrically mounted within nipple 522 in communication with nipple 552A. The distal end of overflow tube 556 is mounted on and preferably bonded to nipple 560 to thus communicate with nipple 552A.

The proximal end of inspiratory tube 502 is preferably removably mounted on nipple 562 of Inspiratory Valve fitting 563 to enable the tube 502 to be coupled to the heated humidifier apparatus showing in FIGS. 3 and 4. The heated humidifier apparatus is of conventional design and preferably includes a single use cartridge.

Detachable patient circuit 500 also preferably includes an end expiratory monitoring tube 564 threaded through the expiratory tube 504 extending from beyond the port 510 in the Y-piece 505 to the nipple 554A (FIG. 8) past the Expiratory Valve 520.

The connector body 506 is configured so that when it is properly seated on the permanent portion mounting structure 533, all of the nipples 550A, 552A, 554A mate across the detachable/permanent interface, e.g., 80 in FIG. 1, with corresponding tubular openings 550B, 552B, 554B in the mounting structure 633 (FIGS. 9A). Nipple 550B opens to the fresh gas supply port, nipple 552B opens to the overflow tube, and nipple 554B preferably communicates with a tube (not shown) for coupling to various external instruments.

The connector body 506 is additionally configured so that when placed on the permanent portion mounting structure, it is automatically latched in place and cannot be removed until the aforementioned Eject button, e.g. 238 in FIG. 3, is depressed.

Attention is now particularly directed to FIG. 9A which illustrates the structural interface between the connector body 506 and the permanent portion mounting structure 533. The mounting structure 533 includes a slide member 572 connected to an axial pin 574 associated with a pneumatic cylinder 576. Note that the pin 574 and cylinder 576 respectively correspond to the pin 244 and cylinder 242 referred to in FIG. 3. The pin 574 is axially spring urged to the left (as see in FIG. 9A) and is moved to the right when the cylinder 576 is actuated. Note that the slide 572 has a first inclined surface 580. Also note that the slide 572 includes a projecting latch member 582 having an inclined upper surface 584. A pin 586, associated with a Valve Body 590 is located beneath the latch member 582. The pin 586 and Valve Body 590 correspond respectively to pin 217 and Seated Sensor Valve 216 previously discussed in connection with FIG. 3. When the pin 586 is in the position depicted in FIG. 9A, the Seated Sensor Valve 366 is open.

The connector body 506 further includes a depending member 594 having a ramp surface 596. The member 594 is undercut to define a slot 598 for receiving the latch member 582. The member 594 terminates in a projection 702 having a flat surface 704.

With reference to FIG. 9A, assume now that the connector body 606 is lowered onto the mounting structure 670, with the nipples 550A, 552A, 554A respectively extending into tubular openings 550B, 552B, 554B, as represented by the arrow 500. As the connector body is lowered, the flat portion 704 of the depending ramp member 694 will contact the inclined surface 684 of the latch member 682 to thus move the slide 672 to the right against its spring arguing. After the projection 702 moves past the latch member 682, the spring bias will force the slope 672 to the left moving the latch member 682 into the slot 698 to the connector body. With connector body 606 so latched to the mounting structure 670, as a consequence of the interference between the latch member 682 and projection 702, the connector body, once seated, cannot be manually removed. Note also that as a consequence of placing the connector body 606 on the mounting structure 670, the pin 686 is depressed by flat portion 704 to thus open SEATED SENSOR VALVE (e.g., 216 of FIG. 3). With the connector body 506 so mated to the reusable mounting structure 533, the aforementioned nipples 550A, 552A, and 554A will be automatically mated to the tubular openings 552B, 552B and 554B on the reusable portion.

Figure 9B:
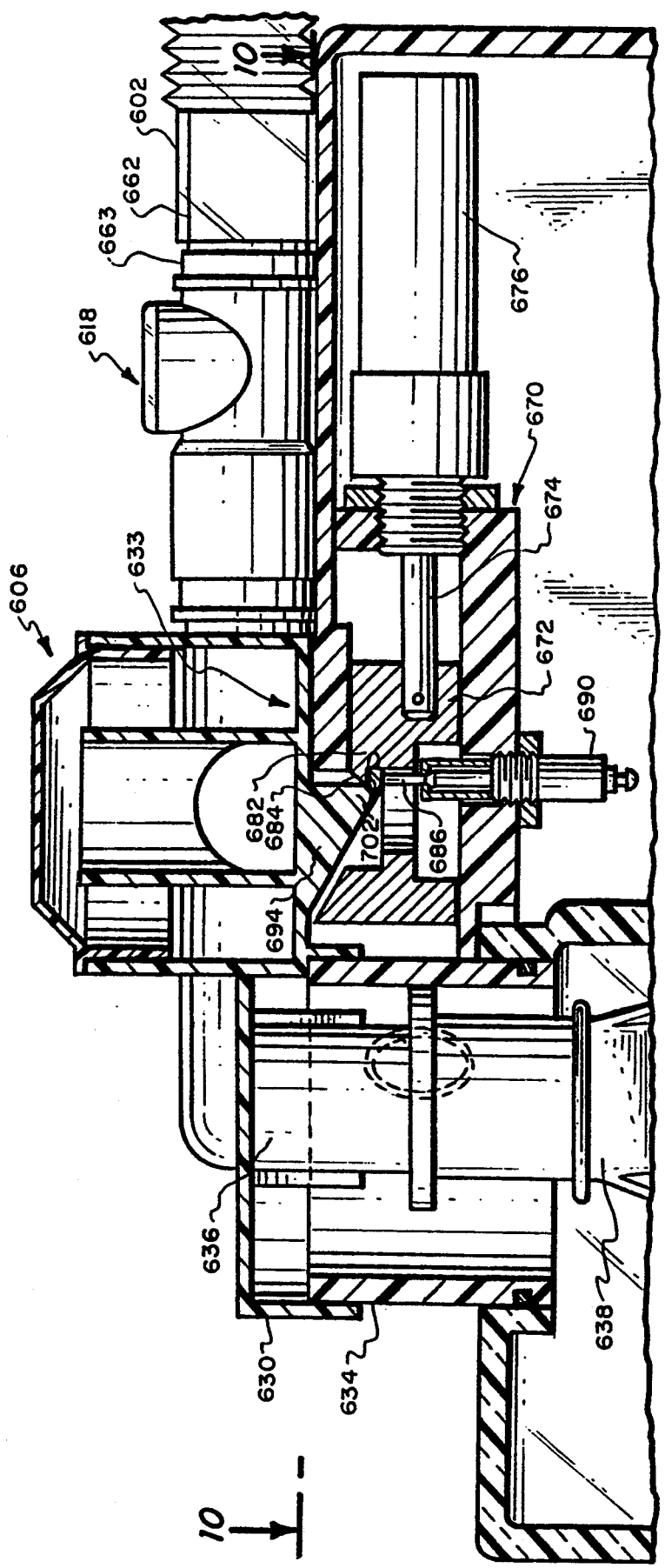
Figure 10:
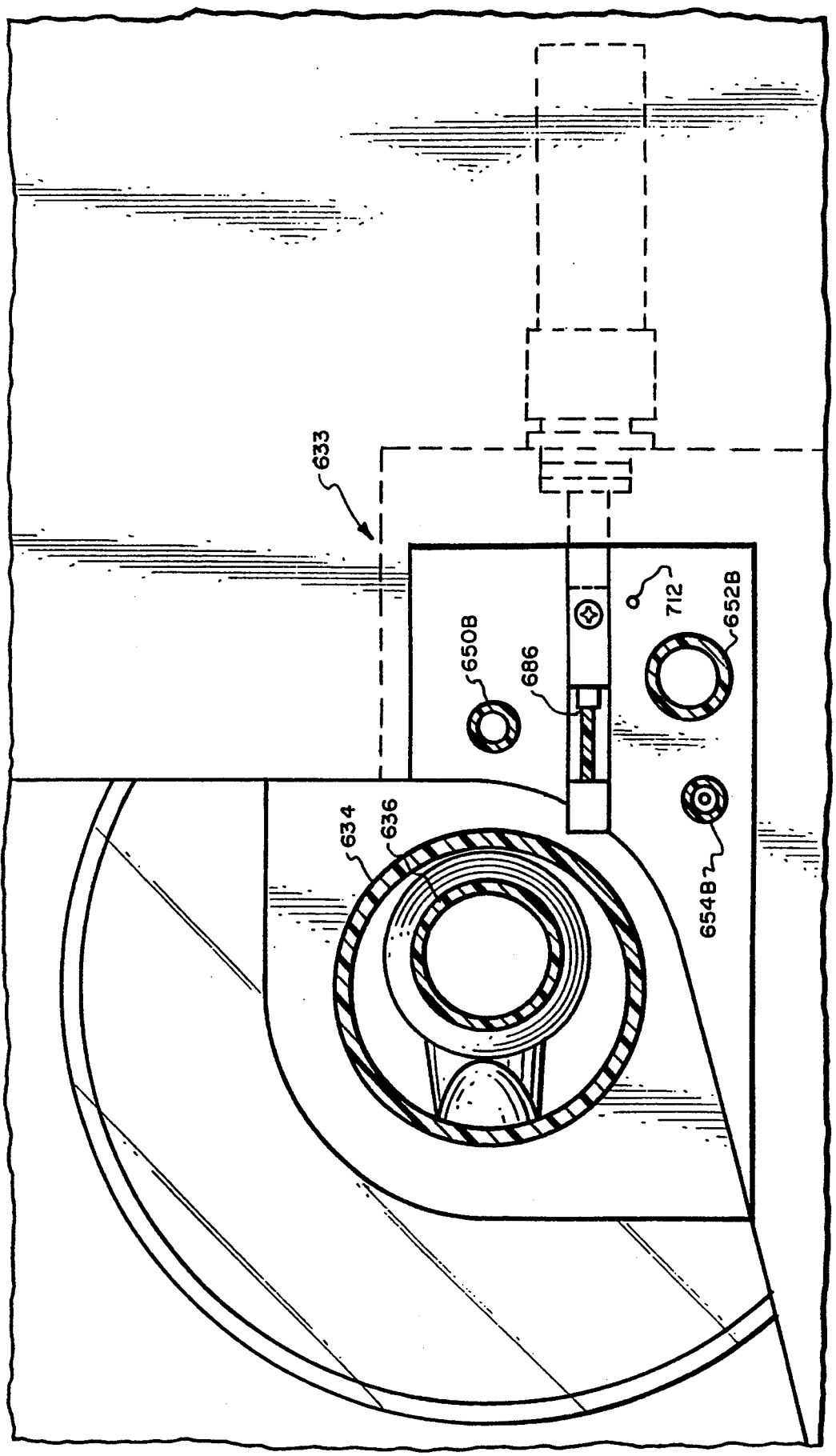
FIG. 10 is a sectional view taken substantially along the plane 10—10 of FIG. 9B showing the connector body of the detachable portion latched to the structural mounting interface of the system's permanent portion.

In order to unlatch the connector body 506, it will be recalled from that the Eject button 238 (FIG. 3) is depressed to actuate the Eject cylinder 242. The schematically illustrated Eject cylinder 242 corresponds to the structural cylinder 676 (FIGS. 9A, 9B). Actuation of the cylinder 676 pulls the axial pin 674 to the right thus pulling the latch member 682 out of the slot 698 thereby freeing the projection 702 enabling the connector body 606 to be lifted from the reusable mounting structure 670.

Figure 11:
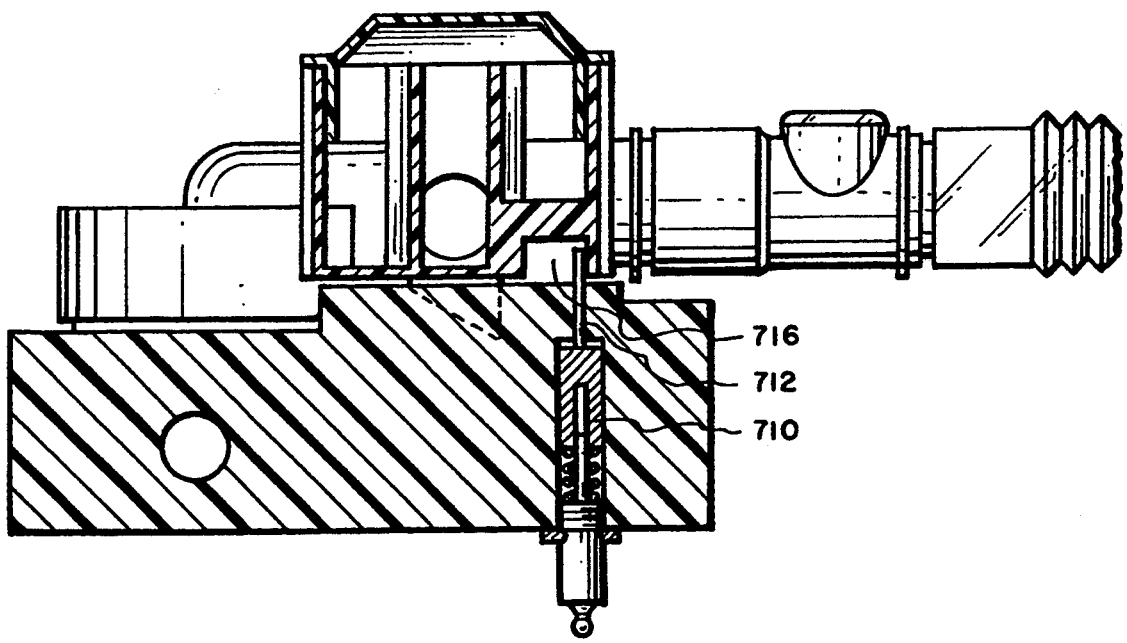
FIG. 11 is a sectional view taken substantially along the plane 11—11 of FIG. 8 showing a seated adult patient circuit.

The foregoing description of FIGS. 6, 7, 8, 9A, 9B, and 10 is substantially identical to that contained in U.S. Pat. No. 4,991,576. In accordance with the present invention, the mounting structure 533 is modified to accommodate the Pediatric Circuit Sensor (e.g., 314 in FIG. 3). More particularly note in FIGS. 10 and 11, the incorporation of Valve 710 having a spring urged actuator pin 712. The Valve 710 and pin 712 correspond, for example, to the Pediatric Circuit Sensor Valve 314 and pin 315 of FIG. 3. The pin 712 is located on the mounting structure such that a recess 716 formed in the underside of a detachable adult patient circuit aligns with the pin when seated as shown in FIGS. 8 and 11. With the pin 712 extended into the recess 716, the Valve 710 is open allowing the aforementioned full patient bag sensing subsystem to operate to hold the Patient Pop-Off Valve closed unless the patient bag is full.

Figure 12:
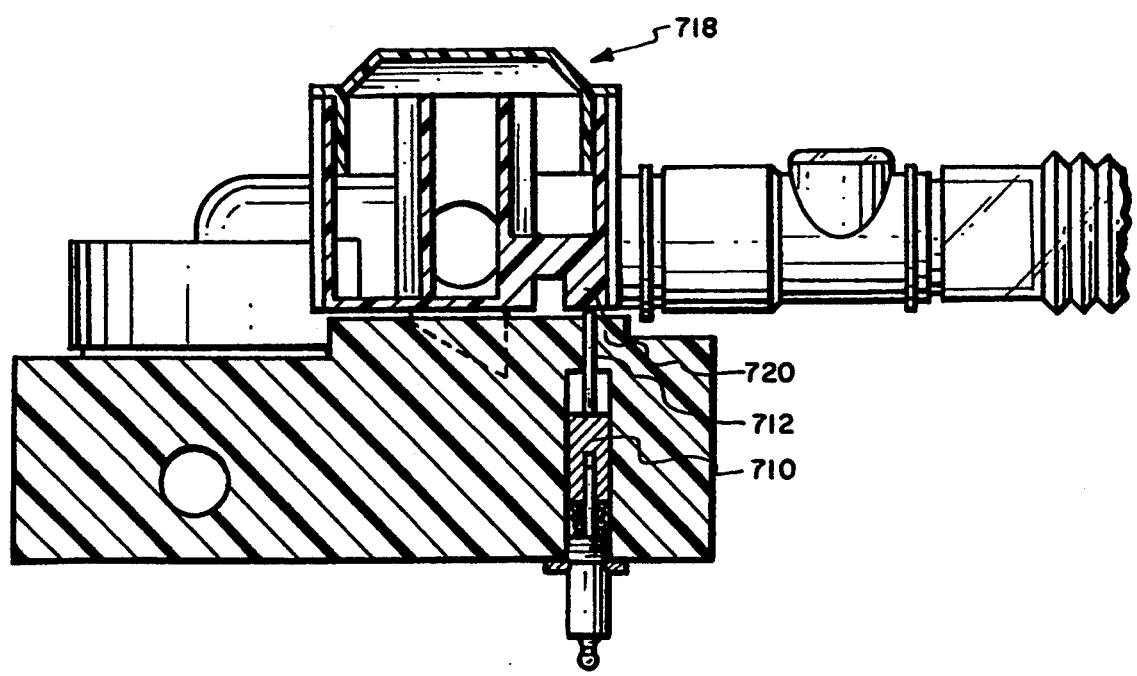
FIG. 12 is a sectional view similar to that of FIG. 8 but showing a seated pediatric patient circuit and the Pediatric Circuit Sensor actuated.

A pediatric breathing circuit 718 (FIG. 12) in accordance with the invention, has its recess 716 at least partially occluded by surface 720 (represented by dashed line 720 in FIG. 8). The surface 720 is located so as to depress pin 712, as shown in FIG. 12, when the pediatric circuit 718 is seated on the mounting structure 633. With the pin 712 depressed, the NO port of Pediatric Circuit Sensor is closed thus cutting off the gas supply to the Patient Pop-Off Valve hold down cylinders (320 in FIG. 3 and 556 in FIG. 4). It is pointed out that the pediatric breathing circuit 718 depicted in FIG. 12 is preferably, though not necessarily, a 2-tube circuit, as distinguished from the 3-tube circuits illustrated in FIGS. 6–9. The distinctions between these two types of circuits is discussed in U.S. Pat. No. 4,991,576.

From the foregoing, it should now be appreciated that improvements in anesthesia gas delivery systems have been disclosed herein primarily for enhancing safe operation and increasing the efficiency of anesthesia gas usage. Although preferred implementations have been described, it should be understood that various alternatives can be readily used without departing from the spirit of the invention or the intended scope of the appended claims. For example only, it should be readily recognized that various alternative exist for implementing full patient reservoir sensing and pediatric breathing circuit sensing. Such alternatives could, for example, include the utilization of other types of sensing devices such as magnetic, capacitive, photoconductive, etc.

We claim:

1. An anesthesia gas delivery system including:
   a patient airway communication device;
   a breathing tube having a first port coupled to said patient airway communication device and a second port comprising a fresh gas inlet port;
   an overflow tube having a first port coupled to said breathing tube and a second port comprising a patient overflow port;
   a variable volume patient reservoir having an entrance opening coupled to said breathing tube proximate to the second port thereof;
   a patient overflow valve having an inlet port coupled to said patient overflow port; and
   a control subsystem including a valve closure device for maintaining said patient overflow valve closed at all times except when said patient reservoir is full, said subsystem including a sensing device responsive to said patient reservoir being full for disabling said valve closure device.

2. The system of claim 1 wherein said control subsystem includes:
   sensor means for determining whether said reservoir is of a first or second type; and wherein
   said control subsystem is operative to maintain said patient overflow valve closed only if said reservoir is of said first type.

3. The system of claim 1 further including:
   a first bias means for establishing a first positive threshold pressure against which a patient breathes.

4. The system of claim 3 further including:
   a second bias means incorporated in series with said patient overflow valve for establishing a second positive threshold pressure against which a patient breathes.

5. The system of claim 4 further including:
   means for setting said first and second positive threshold pressures at substantially the same level.

6. An anesthesia system for coupling a fresh gas supply means to a patient's airway, said system including:
   a detachable structural portion including a connector body defining a fresh gas interface port and a patient overflow interface port;
   a permanent structural portion including a mounting structure defining a fresh gas interface port and a patient overflow interface port;
   said connector body being configured to detachably seat on said mounting structure with said fresh gas interface ports communicating with one another and said patient overflow interface ports communicating with one another;
   said detachable portion including:
      a patient airway communication device;
      a breathing tube having a first port coupled to said patient airway communication device and a second port coupled to said connector body fresh gas interface port;
      an overflow tube having a first end coupled to said breathing tube and a second end coupled to said patient overflow interface port; and
      a variable volume patient reservoir having an entrance opening coupled to said breathing tube proximate to the second port thereof;
   said permanent portion including:
      a patient overflow valve having an inlet port coupled to said permanent portion patient overflow interface port; and
      a control subsystem including a valve closure device for maintaining said patient overflow valve closed at all times except when said reservoir is full, said subsystem including a sensing device responsive to said patient reservoir being full for disabling said valve closure device.

7. The system of claim 6 including a sensor indicating when said connector body is seated on said mounting structure; and
   a valve permitting gas flow into said connector body fresh gas interface port only when said connector body is seated.

8. The system of claim 6 including sensor means for disabling said control subsystem when a pediatric size detachable portion is seated on said mounting structure.

9. The system of claim 6 further including:
   a source of fresh gas;
   a scavenging port; and
   a fresh gas valve operable in a default state to couple said fresh gas source to said scavenging port and in an actuated state to couple said fresh gas source to said permanent portion fresh gas interface port.

10. The system of claim 6 further including:
    a constant volume container;
    means in communication with said container for varying the pressure therein; and
    means mounting said variable volume patient reservoir in said container whereby pressure variations therein will produce corresponding variations in said reservoir.

11. The system of claim 10 further including:
    an exit path for gas displaced from said container;
    a first biased valve in said exit path for establishing a first positive pressure against which a patient breathes; and a second biased valve mounted in series with said patient overflow valve for establishing a second positive pressure against which a patient breathes.

12. The system of claim 11 further including:
means for setting said first and second positive pressures at substantially the same level.

13. An anesthesia system for coupling a fresh gas supply means to a patient's airway, said system including:
a detachable structural portion including connector body means defining a fresh gas interface port and a patient overflow interface port;
a permanent structural portion including mounting structure means defining a fresh gas interface port and a patient overflow interface port;
means for detachably connecting said connector body means and said mounting structure means for communicating said fresh gas interface ports to one another and said patient overflow interface ports to one another;
said detachable portion including:
patient airway communication means;
breathing tube means having a first port coupled to said patient airway communication means and a second port coupled to said detachable portion fresh gas interface port;
overflow tube means having a first end coupled to said breathing tube means and a second end coupled to said detachable portion patient overflow interface port; and
a patient breathing bag having an entrance opening coupled to said breathing tube means proximate to the second port thereof;
said permanent portion including:
a patient overflow valve having an inlet port coupled to said detachable portion patient overflow interface port; and
control means for establishing the level of pressure at said inlet port for opening said patient overflow valve means;
said control means including:
a rigid container;
means in communication with said container for varying the pressure therein;
means mounting said patient breathing bag in said container whereby pressure variations therein will produce corresponding variations in said patient breathing bag; and
a control subsystem including a valve closure device for maintaining said patient overflow valve closed at all times except when said patient breathing bag is full volume, said subsystem including a sensing device responsive to said patient breathing bag being full for disabling said valve closure device.

14. The system of claim 13 including a sensor indicating when said connector body is seated on said mounting structure; and
a valve permitting gas flow into said connector body fresh gas interface port only when said connector body is seated.

15. The system of claim 13 further including sensor means for determining whether said detachable portion is of a first or second type; and wherein
said sealing means is operative to prevent gas flow through said patient overflow valve only if said detachable portion is of said first type.

16. The system of claim 15 wherein said sensor means includes a pin extending from said mounting structure and movable to either a first or second position; and wherein
said detachable portion connect body is configured to set the position of said pin in accordance with whether said detachable portion is of said first or second type.

17. The system of claim 13 further including:
a source of fresh gas;
a scavenging port; and
a fresh gas valve operable in a default state to couple said fresh gas source to said scavenging port and in an actuated state to couple said fresh gas source to said permanent portion fresh gas interface port.

18. The system claim 13 further including:
an exit path for gas displaced from said container;
a first biased valve in said exit path for establishing a first positive pressure against which a patient breathes; and
a second biased valve mounted in series with said patient overflow valve for establishing a second positive pressure against which a patient breathes.

19. In an anesthesia system including a patient circuit for coupling a fresh gas supply to a patient's airway wherein said patient circuit includes valve means for venting gas from the patient circuit and a variable volume reservoir means for alternately (1) receiving gas during patient exhalation and (2) supplying stored gas during patient inhalation, the improvement comprising:
a constant volume container means for accommodating said variable volume reservoir means;
exit path means for passing gas displaced from said container means;
first bias means for establishing a positive end expiratory pressure against which a patient breathes, said first bias means defining a first positive threshold pressure only above which said exit path means passes gas from said container means; and
second bias means incorporated in series with said valve means for establishing a second positive end expiratory pressure.

20. The system of claim 19 wherein said first bias means comprises a valve having an inlet and an outlet and including a diaphragm movable between first and second positions respectively closing and opening communication between said inlet and outlet; and
means for applying said first positive threshold pressure to said first bias means diaphragm.

21. The system of claim 20 wherein said second bias means comprises a valve having an inlet and an outlet and including a diaphragm movable between first and second positions respectively closing and opening communication between said inlet and outlet; and wherein
said means for applying said first threshold pressure to said first bias means diaphragm applies an equal threshold pressure to said second bias means diaphragm.

* * * * *